US011359226B2

(12) United States Patent
Steemers et al.

(10) Patent No.: US 11,359,226 B2
(45) Date of Patent: Jun. 14, 2022

(54) CONTIGUITY PARTICLE FORMATION AND METHODS OF USE

(71) Applicant: ILLUMINA, INC., San Diego, CA (US)

(72) Inventors: Frank J. Steemers, Encinitas, CA (US); Ramesh Ramji, San Diego, CA (US); Steven Norberg, La Mesa, CA (US); Lena Christiansen, San Diego, CA (US); Dmitry K. Pokholok, San Diego, CA (US); Fan Zhang, San Diego, CA (US)

(73) Assignee: ILLUMINA, INC., San Diego, CA (US)

( * ) Notice: Subject to any disclaimer, the term of this patent is extended or adjusted under 35 U.S.C. 154(b) by 0 days.

(21) Appl. No.: 16/384,741

(22) Filed: Apr. 15, 2019

(65) Prior Publication Data

US 2019/0352591 A1 Nov. 21, 2019

Related U.S. Application Data

(60) Provisional application No. 62/660,452, filed on Apr. 20, 2018.

(51) Int. Cl.
| | | |
|---|---|---|
| *C12Q 1/6806* | (2018.01) | |
| *A61K 47/58* | (2017.01) | |
| *A61K 47/69* | (2017.01) | |
| *C12M 1/12* | (2006.01) | |
| *C12N 5/00* | (2006.01) | |
| *C12N 5/16* | (2006.01) | |

(52) U.S. Cl.
CPC ............ *C12Q 1/6806* (2013.01); *A61K 47/58* (2017.08); *A61K 47/6937* (2017.08); *C12M 25/16* (2013.01); *C12N 5/0012* (2013.01); *C12N 5/16* (2013.01); *C12N 2533/40* (2013.01)

(58) Field of Classification Search
CPC .... C12M 25/16; A61K 47/58; A61K 47/6937; C12N 5/0012; C12N 5/16; C12N 2533/40; C12N 15/1006; C12N 2533/30; G01N 1/36; G01N 33/48; G01N 33/50; G01N 33/5005; C12Q 1/6806; C12Q 1/02
See application file for complete search history.

(56) References Cited

U.S. PATENT DOCUMENTS

| | | |
|---|---|---|
| 5,130,238 A | 7/1992 | Malek |
| 5,185,243 A | 2/1993 | Ullman |
| 5,455,166 A | 10/1995 | Walker |
| 5,573,907 A | 11/1996 | Carrino |
| 5,679,524 A | 10/1997 | Nikiforov |
| 5,958,451 A * | 9/1999 | Chen .................. A61K 9/4825 424/451 |
| 6,210,891 B1 | 4/2001 | Nyren |
| 6,214,587 B1 | 4/2001 | Dattagupta |
| 6,258,568 B1 | 7/2001 | Nyren |
| 6,274,320 B1 | 8/2001 | Rothberg |
| 6,355,431 B1 | 3/2002 | Chee |
| 6,890,741 B2 | 5/2005 | Fan |
| 6,913,884 B2 | 7/2005 | Stuelpnagel |
| 7,001,792 B2 | 2/2006 | Sauer |
| 7,057,026 B2 | 6/2006 | Barnes |
| 7,115,400 B1 | 10/2006 | Adessi |
| 7,211,414 B2 | 5/2007 | Hardin |
| 7,244,559 B2 | 7/2007 | Rothberg |
| 7,315,019 B2 | 1/2008 | Turner |
| 7,329,492 B2 | 2/2008 | Hardin |
| 7,405,281 B2 | 7/2008 | Xu |
| 7,582,420 B2 | 9/2009 | Oliphant |
| 7,595,883 B1 | 9/2009 | Gamal |
| 7,611,869 B2 | 11/2009 | Fan |
| 7,670,810 B2 | 3/2010 | Gunderson |
| 7,985,565 B2 | 7/2011 | Mayer |
| 2005/0053980 A1 | 3/2005 | Gunderson |
| 2005/0181440 A1 | 8/2005 | Chee |
| 2005/0191698 A1 | 9/2005 | Chee |
| 2006/0013784 A1 * | 1/2006 | Philippe .................. A61K 8/46 424/70.5 |
| 2008/0108082 A1 | 5/2008 | Rank |
| 2009/0026082 A1 | 1/2009 | Rothberg |
| 2009/0127589 A1 | 5/2009 | Rothberg |
| 2009/0186349 A1 | 7/2009 | Gunderson |
| 2010/0137143 A1 | 6/2010 | Rothberg |

(Continued)

FOREIGN PATENT DOCUMENTS

| | | |
|---|---|---|
| CA | 3047328 | 6/2018 |
| EP | 0320308 | 6/1989 |

(Continued)

OTHER PUBLICATIONS

Ronaghi et al. (Analytical Biochemistry. 1996. 242: 84-9). (Year: 1996).*
Bigdeli, S et al. A simple method for encapsulating single cells in alginate microspheres allows for direct PCR and whole genome amplification. PLoS One. 2015. 10(2): e011738. 15 pages. (Year: 2015).*
Augst, AD et al. Alginate hydrogels as biomaterials. Macromolecular Bioscience. 2006. 6: 623-633. (Year: 2006).*
Trivedi, V et al. Microfluidic encapsulation of cells in alginate capsules for high throughput screening. 31st Annual International Conference of the IEEE EMBS. Minneapolis, Minnesota, USA. Sep. 2-6, 2009. 2009: 7037-7040. (Year: 2009).*

(Continued)

*Primary Examiner* — Renee Claytor
*Assistant Examiner* — Susan E. Fernandez
(74) *Attorney, Agent, or Firm* — Knobbe, Martens, Olson & Bear LLP

(57) ABSTRACT

Embodiments of systems, methods, and compositions provided herein relate to hollow beads encapsulating single cells. Some embodiments include performing multiple co-assays on a single cell encapsulated within a hollow bead, including nucleic acid sequencing, preparing nucleic acid libraries, determining methylation status, identifying genomic variants, or protein analysis.

11 Claims, 12 Drawing Sheets

Specification includes a Sequence Listing.

(56) References Cited

U.S. PATENT DOCUMENTS

| | | | |
|---|---|---|---|
| 2010/0282617 A1 | 11/2010 | Rothberg | |
| 2012/0129954 A1* | 5/2012 | Falcone | A61L 27/54 |
| | | | 514/781 |
| 2015/0071997 A1* | 3/2015 | Garcia | A61K 9/5031 |
| | | | 424/457 |
| 2015/0157569 A1* | 6/2015 | Shum | A61K 9/107 |
| | | | 424/9.1 |
| 2015/0284768 A1* | 10/2015 | Craig | C12Q 1/6806 |
| | | | 506/26 |
| 2015/0376609 A1 | 12/2015 | Hindson et al. | |
| 2016/0271064 A1 | 9/2016 | Sell et al. | |
| 2019/0249171 A1 | 8/2019 | Wu et al. | |

FOREIGN PATENT DOCUMENTS

| | | | |
|---|---|---|---|
| EP | 0336731 | | 10/1989 |
| EP | 0439182 | | 7/1991 |
| JP | 2016-517281 | | 6/2016 |
| KR | 10-2017-0020704 | | 2/2017 |
| RU | 2603745 C2 | | 11/2016 |
| WO | WO 1989/09835 | | 10/1989 |
| WO | WO 1989/12696 | | 12/1989 |
| WO | WO 1990/01069 | | 2/1990 |
| WO | WO 1991/06678 | | 5/1991 |
| WO | WO 2004/018497 | | 6/2004 |
| WO | WO 2006/125458 | | 11/2006 |
| WO | WO 2007/123744 | | 11/2007 |
| WO | WO 2008/109176 | | 9/2008 |
| WO | WO 2012/058096 | | 5/2012 |
| WO | WO 2014/145555 | | 9/2014 |
| WO | WO 2014/189957 | | 11/2014 |
| WO | WO 2015/048173 | | 4/2015 |
| WO | WO 2015/088299 | | 6/2015 |
| WO | WO 2015/147147 | | 10/2015 |
| WO | WO 2015/200893 | | 12/2015 |
| WO | WO 2016/004234 | | 1/2016 |
| WO | WO-2016130704 A2 * | 8/2016 | ........... C12Q 1/6806 |
| WO | WO 2017/013138 | | 1/2017 |
| WO | WO 2017/040024 A1 | | 3/2017 |
| WO | WO 2017/075265 | | 5/2017 |
| WO | WO 2017/100347 | | 6/2017 |
| WO | WO 2018/071448 A1 | | 4/2018 |
| WO | WO 2018/119301 | | 6/2018 |
| WO | WO 2018/140966 | | 8/2018 |
| WO | WO 2019/028047 | | 2/2019 |
| WO | WO 2019/028166 | | 2/2019 |
| WO | WO 2019/160820 | | 8/2019 |

OTHER PUBLICATIONS

Elbert, DL et al. Protein delivery from materials formed by self-selective conjugate additions reactions. Journal of Controlled Release. 2001. 76: 11-25. (Year: 2001).*
Search Report issued in RU application No. 2019144343, dated Jun. 21, 2020.
Appleby et al. (Methods Mol Biol. 2009; 513:19-39).
Bentley et al., Nature 456:53-59 (2008).
Cockroft et al. J. Am. Chem. Soc. 130, 818-820 (2008).
Deamer et al. Trends Biotechnol. 18, 147-151 (2000).
Deamer et al. Acc. Chem. Res. 35:817-825 (2002).
Dean et al., Proc. Natl. Acad. Sci. USA 99:5261-66 (2002).
Fox et al. (Methods Mol Biol. 2009;553:79-108).
Grothues et al. Nucleic Acids Res. 21(5):1321-2 (1993).
Healy, Nanomed. 2, 459-481 (2007).
Korlach et al. Proc. Natl. Acad. Sci. USA 105, 1176-1181 (2008).
Lage et al., Genome Research 13:294-307 (2003).
Levene et al. Science 299, 682-686 (2003).
Li et al. Nat. Mater. 2:611-615 (2003).
Lizardi et al., Nat. Genet. 19:225-232 (1998).
Lundquist et al. Opt. Lett. 33, 1026-1028 (2008).
Margulies et al. (Nature 2005 437: 376-80).
Morozova et al. (Genomics. 2008 92:255-64).
Ronaghi et al. (Analytical Biochemistry 1996 242: 84-9).
Ronaghi et al. Science 281 (5375), 363 (1998).
Ronaghi, Genome Res. 11(1), 3-11 (2001).
International Search Report and Written Opinion issued in patent application No. PCT/US2019/027540, dated Jul. 24, 2019.
Decision to Grant issued in RU application No. 2019144343, dated Apr. 27, 2021.
Office Action issued in JP application No. 2019-568626, dated Feb. 2, 2021.
Shupletsova et al., "Encapsulation of cells and tissues of the pancreas: problems and ways to overcome them", Genes and cells, vol. XI, N 1, 2016, pp. 18-23.
Search Report issued in AU application No. 2019220559, dated Mar. 12, 2021.
Search Report issued in AU application No. 2018312560, dated Mar. 11, 2021.
Office Action issued in EP application No. 18755643.6, dated May 10, 2021.
Search Report issued in AU application No. 2019220559, dated May 18, 2021.
Freeman et al: "Single-cell genome sequencing at ultra-high-throughput with microfluidic droplet barcoding. (includes Online Methods)", 1-7, 24-33, Nature Biotechnology, vol. 35, No. 7, Jul. 1, 2017 (Jul. 1, 2017) pp. 640-646, 4pp.
Rakszewska et al. (Angewandte Chemie, 2016, 55:6698-6701) (Year: 2016).
Search Report and Written Opinion issued in application No. PCT/US2019/057852, dated Jan. 16, 2020.
Shendure et al. (Science 2005 309: 1728-32).
Soni et al. Clin. Chem. 53, 1996-2001 (2007).
Tan et al , Heterogeneous multi-compartmental hydrogel particles as synthetic cells for incompatible tandem reactions, 2017, Nature Communications, 8,663, pp. 1-10 (Year: 2017).
Trivedi et al. Microfluidic encapsulation of cells in alginate capsules for high throughput screening. 31st Annual International Conference of the IEEE EMBS. Minneapolis, Minnesota, USA. Sep. 2-6, 2009. 2009: 7037-7040. (Year: 2009).
Vitak et al. Nat Meth. 2017;14:302-308.
Walker et al., Nucl. Acids Res. 20:1691-96 (1992).
Garni, Biopores/membrane proteins in synthetic polymer membranes, Biochimica et Biophysica Acta, 1859, 2017, 619-638.
Office Action issued in JP application No. 2019-568626, dated Jun. 22, 2021.

* cited by examiner

- ▲ Protein
- ■ Glycans
- ● Small molecule
- ⬭ Reactive group
- Y Antibody or binding molecule
- ⌇ + Polymer
- ⌇ - Polymer

CONTIGUITY PARTICLE FORMATION AND METHODS OF USE

CROSS-REFERENCE TO RELATED APPLICATIONS

This application claims priority to U.S. Provisional Application No. 62/660,452, filed on Apr. 20, 2018, which is hereby incorporated by reference in its entirety.

REFERENCE TO SEQUENCE LISTING

The present application is being filed along with a Sequence Listing in electronic format. The Sequence Listing is provided as a file entitled Sequence_Listing_ILLINC_395A, created on Apr. 15, 2019, which is 2,498 bytes in size. The information in the electronic format of the Sequence Listing is incorporated herein by reference in its entirety.

FIELD

Systems, methods, and compositions provided herein relate to hollow beads encapsulating a single cell, methods making the hollow beads, and methods of using the hollow beads for conducting multiple co-assays on the encapsulated cell, including, for example, spatial index sequencing and nucleic acid library preparation.

BACKGROUND

The detection of specific nucleic acid sequences present in a biological sample has been used, for example, as a method for identifying and classifying microorganisms, diagnosing infectious diseases, detecting and characterizing genetic abnormalities, identifying genetic changes associated with cancer, studying genetic susceptibility to disease, and measuring response to various types of treatment. A common technique for detecting specific nucleic acid sequences in a biological sample is nucleic acid sequencing.

Next generation sequencers are powerful tools that generate large amounts of genomic data per sequencing run. Interpreting and analyzing this large amount of data can be challenging. Single cell DNA sequencing is emerging as one tool for studying genomic heterogeneity. Specifically, the microbiome, which carries multiple repeated genomic regions, can be sequenced by obtaining DNA sequences from only a single cell. Performing multiple enzymatic reactions on a single cell is unreliable due to the challenges in confining and accessing intracellular biomolecules within a single cell over multiple assays. For example, many cell based assays fail to secure intracellular molecules, resulting in loss of biomolecules during performance of the assay.

SUMMARY

The present disclosure is related to systems, methods, and compositions for performing multiple co-assays on a single cell, wherein the single cell is encapsulated within a hollow bead, such that the single cell is confined in order to perform multiple co-assays, including, for example, lysis, DNA analysis, RNA analysis, protein analysis, tagmentation, nucleic acid amplification, nucleic acid sequencing, DNA library preparation, assay for transposase accessible chromatic using sequencing (ATAC-seq), contiguity-preserving transposition (CPT-seq), single cell combinatorial indexed sequencing (SCI-seq), or single cell genome amplification, or any combination thereof performed sequentially on a single cell.

Some embodiments provided herein relate to a hollow bead encapsulating a single cell. In some embodiments, the hollow bead includes a polymer shell and a single cell disposed within the polymer shell. In some embodiments, the polymer shell includes pores that allow diffusion of a reagent through the polymer shell while retaining the single cell.

Further embodiments relate to a method of performing multiple sequential co-assays on a single cell encapsulated within a hollow bead. In some embodiments, the method includes obtaining a hollow bead as described herein, wherein the hollow bead encapsulates a single cell and sequentially contacting the single cell with reagents to perform multiple sequential co-assays.

Some embodiments provided herein relate to a method of encapsulating a single cell within a hollow bead. In some embodiments, the method includes mixing a single cell with a polymer to form a mixture and mixing the mixture with a crosslinking oil to form a polymer shell encapsulating the single cell, wherein the polymer shell includes pores that allow diffusion of a reagent through the polymer shell while retaining the single cell.

BRIEF DESCRIPTION OF THE DRAWINGS

As shown in FIG. 3, increasing bead porosity can increase the flow of particles into or out of the bead, and controlling the porosity provides control of particles (including particle size) that flow into or out of the bead.

FIG. 7 demonstrates an embodiment of performing tagmentation to generate ATAC-seq fragments, reverse transcription to initiate cDNA synthesis, and PCR reactions to generate an indexed library.

FIG. 8 demonstrates an embodiment of performing tagmentation to generate ATAC-seq fragments, reverse transcription to initiate cDNA synthesis, and PCR reactions with random extension for full length RNA sequencing to generate an indexed library.

FIG. 9 demonstrates a three-tier combinatorial indexing approach using two rounds of indexed split ligation and one round of indexed PCR.

FIG. 10 demonstrates multiple co-assays for combinatorial indexing with indexed transposomes.

FIG. 11 demonstrates multiple co-assays for single cell whole genome amplification.

DETAILED DESCRIPTION

Figure 1:
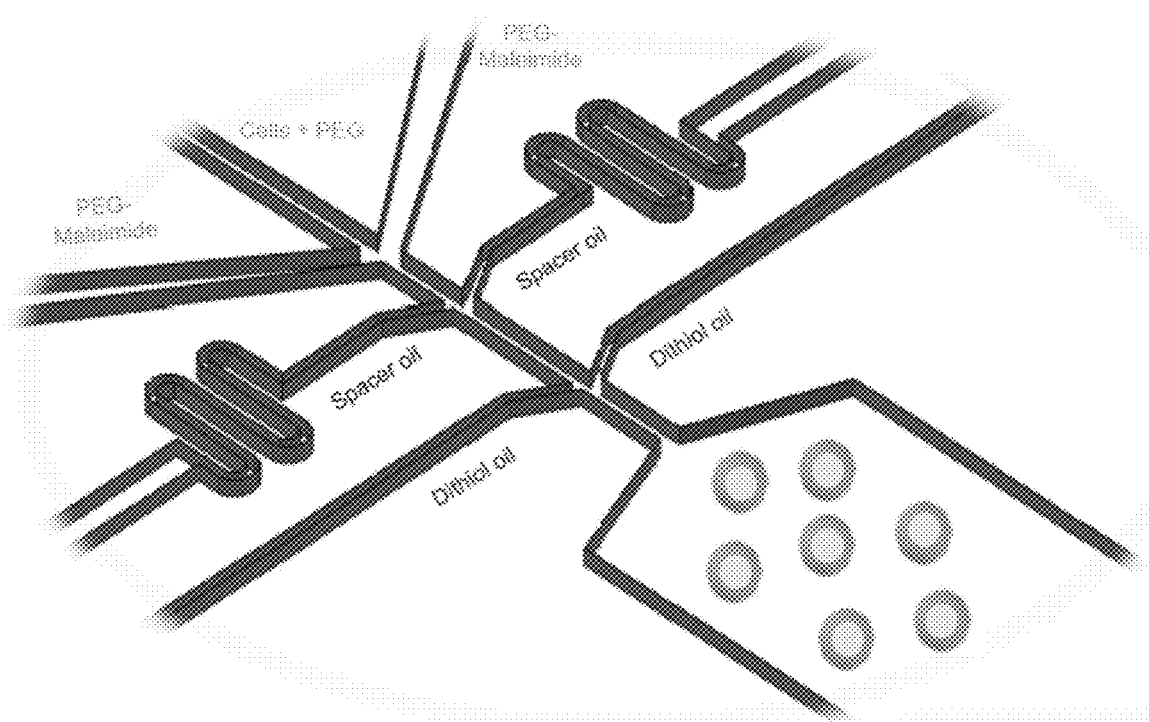
FIG. 1 is a schematic diagram of an embodiment of a microfluidic droplet generator system that can be used to prepare hollow beads encapsulating a cell.

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented herein. It will be readily understood that the aspects of the present disclosure, as generally described herein, and illustrated in the Figures, can be arranged, substituted, combined, separated, and designed in a wide variety of different configurations, all of which are explicitly contemplated herein.

Embodiments provided herein relate to hollow beads encapsulating a single cell, methods of making the hollow beads, and methods of performing multiple co-assays on a single cell encapsulated within a hollow bead. The hollow beads may include hydrogel polymers and crosslinkers that are mixed in the presence of a cell, and which form hollow beads that encapsulate the cell. The hollow beads may include pores that allow diffusion of reagents through the hollow bead while retaining the cell within the hollow bead, thereby allowing reactions to take place within the hollow beads. In some embodiments, the hollow beads enable co-assays to be performed on the same single cell while maintaining cellular contiguity. In particular, the methods, systems, and compositions provided herein allow confining and accessing intracellular biomolecules within the encapsulated cells. Accordingly, in some embodiments, the hollow beads described herein are referred to herein as contiguity particles. Thus, the term "contiguity particle" as used herein refers to a hollow bead encapsulating a single cell.

The contiguity particles described herein may be used for next generation cell compartmentalization approaches and allow multi-analyte assays performed on an individual cell. The contiguity particles and methods of use described herein efficiently allow millions of cells to be analyzed individually thereby reducing the cost of sample preparation and maintaining sample contiguity. The compositions and methods described herein maintain cellular contiguity without the use of external compartmentalization strategies (microfluidics) such as emulsions, immobilization, or other micro-compartments.

In some embodiments, the contiguity particles as described herein can be used in assays to analyze a single cell. Assays that may be performed on the single cell may include, for example, cellular lysis, DNA analysis, RNA analysis, nucleic acid sequencing, protein analysis, tagmentation, nucleic acid amplification, DNA library preparation, assay for transposase accessible chromatic using sequencing (ATAC-seq), contiguity-preserving transposition (CPT-seq), single cell combinatorial indexed sequencing (SCI-seq), or single cell genome amplification, or any combination thereof performed sequentially.

The use of contiguity particles for performing one or more assays on a single cell may be used simultaneously on multiple contiguity particles in order to simultaneously perform co-assays on a number of single cells, for example from 10,000 to 1 million single cells, such as 10,000, 50,000, 100,000, 500,000, or 1 million single cells.

The pore size of the contiguity particle can be engineered to allow the diffusion of reagents, such as enzymes, chemicals, and smaller sized primers (<50 bps), while retaining the single cell itself or while retaining other larger particles, such as larger nucleic acids (>300 bps), inside the hollow bead during the performance of one or more assays.

As used herein, the term "reagent" describes an agent or a mixture of two or more agents useful for reacting with, interacting with, diluting, or adding to a sample, and may include agents used in assays described herein, including agents for lysis, nucleic acid analysis, nucleic acid amplification reactions, protein analysis, tagmentation reactions, ATAC-seq, CPT-seq, or SCI-seq reactions, or other assays. Thus, reagents may include, for example, buffers, chemicals, enzymes, polymerase, primers having a size of less than 50 base pairs, template nucleic acids, nucleotides, labels, dyes, or nucleases. In some embodiments, the reagent includes lysozyme, proteinase K, random hexamers, polymerase (for example, Φ29 DNA polymerase, Taq polymerase, Bsu polymerase), transposase (for example, Tn5), primers (for example, P5 and P7 adaptor sequences), ligase, catalyzing enzyme, deoxynucleotide triphosphates, buffers, or divalent cations.

Contiguity Particles

In some embodiments, the hollow bead has a polymer shell that was prepared from a hydrogel composition. As used herein, the term "hydrogel" refers to a substance formed when an organic polymer (natural or synthetic) is cross-linked via covalent, ionic, or hydrogen bonds to create a three-dimensional open-lattice structure that entraps water molecules to form a gel. In some embodiments, the hydrogel may be a biocompatible hydrogel. As used herein, the term "biocompatible hydrogel" refers to a polymer that forms a gel that is not toxic to living cells and allows sufficient diffusion of oxygen and nutrients to entrapped cells to maintain viability. In some embodiments, the hydrogel material includes alginate, acrylamide, or poly-ethylene glycol (PEG), PEG-acrylate, PEG-amine, PEG-carboxylate, PEG-dithiol, PEG-epoxide, PEG-isocyanate, PEG-maleimide, polyacrylic acid (PAA), poly(methyl methacrylate) (PMMA), polystyrene (PS), polystyrene sulfonate (PSS), polyvinylpyrrolidone (PVPON), N,N'-bis(acryloyl)cystamine, polypropylene oxide (PPO), poly(hydroxyethyl methacrylate) (PHEMA), poly(N-isopropylacrylamide) (PNIPAAm), poly(lactic acid) (PLA), poly(lactic-co-glycolic acid) (PLGA), polycaprolactone (PCL), poly(vinylsulfonic acid) (PVSA), poly(L-aspartic acid), poly(L-glutamic acid), polylysine, agar, agarose, heparin, alginate sulfate, dextran sulfate, hyaluronan, pectin, carrageenan, gelatin, chitosan, cellulose, collagen, bisacrylamide, diacrylate, diallylamine, triallylamine, divinyl sulfone, diethyleneglycol diallyl ether, ethyleneglycol diacrylate, polymethyleneglycol diacrylate, polyethyleneglycol diacrylate, trimethylopropoane trimethacrylate, ethoxylated trimethylol triacrylate, or ethoxylated pentaerythritol tetracrylate, or combinations or mixtures thereof. In some embodiments, the hydrogel is an alginate, acrylamide, or PEG based material. In some embodiments, the hydrogel is a PEG based material with acrylate-dithiol, epoxide-amine reaction chemistries. In some embodiments, the hydrogel forms a polymer shell that includes PEG-maleimide/dithiol oil, PEG-epoxide/amine oil, PEG-epoxide/PEG-amine, or PEG-dithiol/PEG-acrylate. In some embodiments, the hydrogel material is selected in order to avoid generation of free radicals that have the potential to damage intracellular biomolecules. In some embodiments, the hydrogel polymer includes 60-90% fluid, such as water, and 10-30% polymer. In certain embodiments, the water content of hydrogel is about 70-80%. As used herein, the term "about" or "approximately", when modifying a numerical value, refers to variations that can occur in the numerical value. For example, variations can occur through differences in the manufacture of a particular substrate or component. In one embodiment, the term "about" means within 1%, 5%, or up to 10% of the recited numerical value.

As used herein, the polymer shell is a polymer surface of a hollow bead, having a shell with an interior that encapsulates a single cell. Due to the nature of the hollow beads described herein, the contiguity particles can retain genetic material after multiple assays and can be released by physical force, cleaving chemicals, or by generating osmotic imbalance depending on the thickness of the polymer shell.

Hydrogels may be prepared by cross-linking hydrophilic biopolymers or synthetic polymers. Thus, in some embodiments, the hydrogel may include a crosslinker. As used herein, the term "crosslinker" refers to a molecule that can form a three-dimensional network when reacted with the appropriate base monomers. Examples of the hydrogel polymers, which may include one or more crosslinkers, include but are not limited to, hyaluronans, chitosans, agar, heparin, sulfate, cellulose, alginates (including alginate sulfate), collagen, dextrans (including dextran sulfate), pectin, carrageenan, polylysine, gelatins (including gelatin type A), agarose, (meth)acrylate-oligolactide-PEO-oligolactide-(meth)acrylate, PEO-PPO-PEO copolymers (Pluronics), poly(phosphazene), poly(methacrylates), poly(N-vinylpyrrolidone), PL(G)A-PEO-PL(G)A copolymers, poly(ethylene imine), polyethylene glycol (PEG)-thiol, PEG-acrylate, acrylamide, N,N'-bis(acryloyl)cystamine, PEG, polypropylene oxide (PPO), polyacrylic acid, poly(hydroxyethyl methacrylate) (PHEMA), poly(methyl methacrylate) (PMMA), poly(N-isopropylacrylamide) (PNIPAAm), poly(lactic acid) (PLA), poly(lactic-co-glycolic acid) (PLGA), polycaprolactone (PCL), poly(vinylsulfonic acid) (PVSA), poly(L-aspartic acid), poly(L-glutamic acid), bisacrylamide, diacrylate, diallylamine, triallylamine, divinyl sulfone, diethyleneglycol diallyl ether, ethyleneglycol diacrylate, polymethyleneglycol diacrylate, polyethyleneglycol diacrylate, trimethylopropoane trimethacrylate, ethoxylated trimethylol triacrylate, or ethoxylated pentaerythritol tetracrylate, or combinations thereof. Thus, for example, a combination may include a polymer and a crosslinker, for example polyethylene glycol (PEG)-thiol/PEG-acrylate, acrylamide/N,N'-bis(acryloyl)cystamine (BACy), or PEG/polypropylene oxide (PPO). In some embodiments, the polymer shell includes a four-arm polyethylene glycol (PEG). In some embodiments, the four-arm polyethylene glycol (PEG) is selected from the group consisting of PEG-acrylate, PEG-amine, PEG-carboxylate, PEG-dithiol, PEG-epoxide, PEG-isocyanate, and PEG-maleimide In some embodiment, the crosslinker is an instantaneous crosslinker or a slow crosslinker. An instantaneous crosslinker is a crosslinker that instantly crosslinks the hydrogel polymer, and is also referred to herein as click chemistry. Instantaneous crosslinkers may include dithiol oil+PEG-maleimide or PEG epoxide+amine oil. A slow crosslinker is a crosslinker that slowly crosslinks the hydrogel polymer, and may include PEG-epoxide+PEG-amine or PEG-dithiol+PEG-acrylate. A slow crosslinker may take more than several hours to crosslink, for example more than 2, 3, 4, 5, 6, 7, 8, 9, 10, 11, or 12 hours to crosslink. In some embodiments provided herein, contiguity particles are formulated by an instantaneous crosslinker, and thereby preserve the cell state better compared to a slow crosslinker. Without wishing to be bound by theory, cells may possible undergo physiological changes by intracellular signaling mechanisms during longer crosslinking times.

In some embodiments, a crosslinker forms a disulfide bond in the hydrogel polymer, thereby linking hydrogel polymers. In some embodiments, the hydrogel polymers form a hydrogel matrix having pores (for example, a porous hydrogel matrix). These pores are capable of retaining sufficiently large particles, such as a single cell or nucleic acids extracted therefrom within the polymer shell, but allow other materials, such as reagents, to pass through the pores, thereby passing in and out of the hollow beads. In some embodiments, the pore size of the polymer shell is finely tuned by varying the ratio of the concentration of polymer to the concentration of crosslinker. In some embodiments, the ratio of polymer to crosslinker is 30:1, 25:1, 20:1, 19:1, 18:1, 17:1, 16:1, 15:1, 14:1, 13:1, 12:1, 11:1, 10:1, 9:1, 8:1, 7:1, 6:1, 5:1, 4:1, 3:1, 2:1, 1:1, 1:2, 1:3, 1:4, 1:5, 1:6, 1:7, 1:8, 1:9, 1:10, 1:15, 1:20, or 1:30, or a ratio within a range defined by any two of the aforementioned ratios. In some embodiments, additional functions such as DNA primer, or charged chemical groups can be grafted to polymer matrix to meet the requirements of different applications.

As used herein, the term "porosity" means the fractional volume (dimension-less) of a hydrogel that is composed of open space, for example, pores or other openings. Therefore, porosity measures void spaces in a material and is a fraction of volume of voids over the total volume, as a percentage between 0 and 100% (or between 0 and 1). Porosity of the hydrogel may range from 0.5 to 0.99, from about 0.75 to about 0.99, or from about 0.8 to about 0.95.

The polymer shell can have any pore size that allows for sufficient diffusion of reagents while concomitantly retaining the single cell or nucleic acids extracted therefrom. As used herein, the term "pore size" refers to a diameter or an effective diameter of a cross-section of the pores. The term "pore size" can also refer to an average diameter or an average effective diameter of a cross-section of the pores, based on the measurements of a plurality of pores. The effective diameter of a cross-section that is not circular equals the diameter of a circular cross-section that has the same cross-sectional area as that of the non-circular cross-section. In some embodiments, the hydrogel can be swollen when the hydrogel is hydrated. The sizes of the pores size can then change depending on the water content in the hydrogel. In some embodiments, the pores of the hydrogel can have a pore of sufficient size to retain the encapsulated cell within the hydrogel but allow reagents to pass through. In some embodiments, the interior of the polymer shell is an aqueous environment. In some embodiments, the single cell disposed within the polymer shell is free from interaction with the polymer shell and/or is not in contact with the polymer shell. In some embodiments, a polymer shell is formed around a cell (as described herein in greater detail), and the cell is in contact with the polymer shell due to the polymer shell being brought to the cell surface due to passive adsorption or in a targeted manner, such as by being attached to an antibody or other specific binding molecule.

Figure 2:
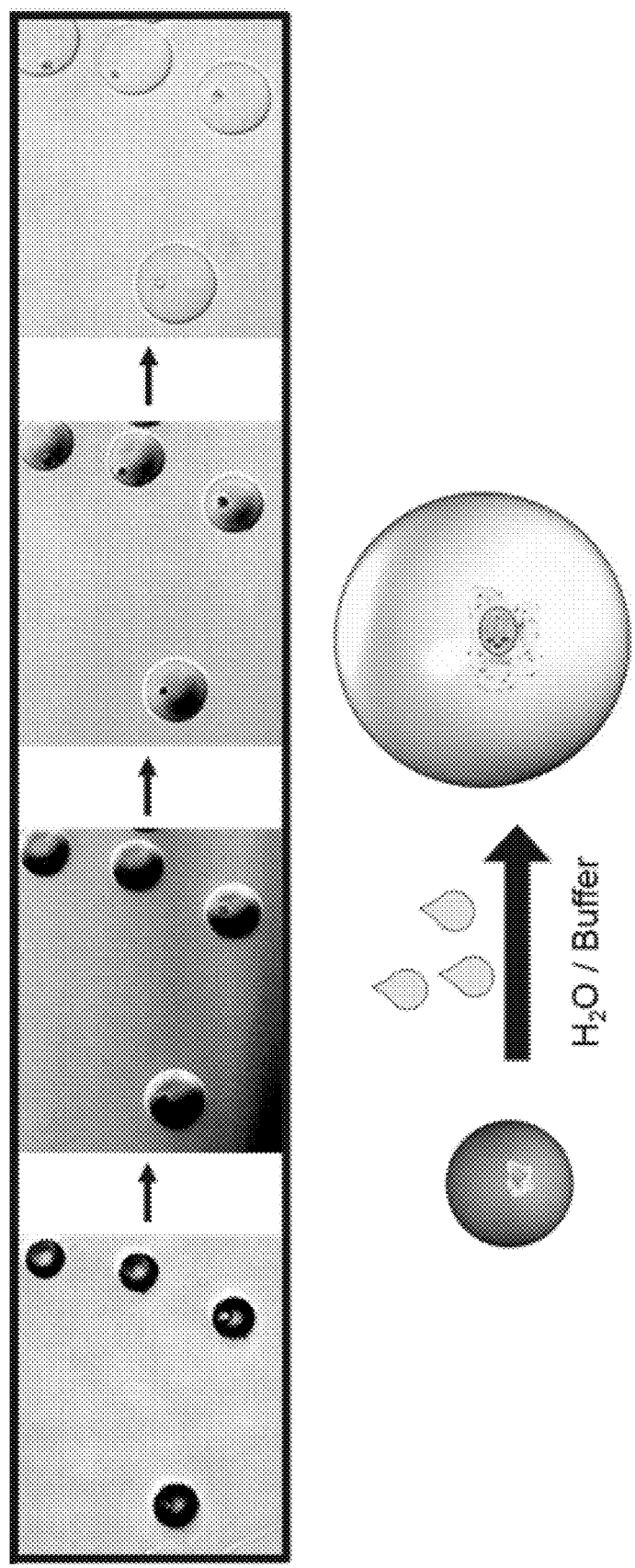
FIG. 2 depicts micrograph images and a schematic representation of an embodiment of hollow beads that are capable of expanding in size in the presence of an aqueous buffer. The micrograph images depict beads in various states, including (from left to right): dehydrated beads; beads initially contacted with an aqueous phase; beads beginning to swell; and completely swollen beads.

In some embodiments, the contiguity particles is of a sufficient size to encapsulate a single cell. In some embodiments, the contiguity particle has a diameter of about 20 µm to about 200 µm, such as 20, 30, 40, 50, 60, 70, 80, 90, 100, 110, 120, 130, 140, 150, 160, 170, 180, 190, or 200 µm, or a diameter within a range defined by any two of the aforementioned values. The size of the contiguity particle may change due to environmental factors. In some embodiments, the contiguity particles expand when they are separated from continuous oil phase and immersed in an aqueous phase, as shown in FIG. 2. In some embodiments, expansion of the contiguity particles increases the efficiency of performing assays on the genetic material inside the encapsulated cells. In some embodiments, expansion of the contiguity particles creates a larger environment for indexed inserts to be amplified during PCR, which may otherwise be restricted in current cell based assays.

Figure 3:
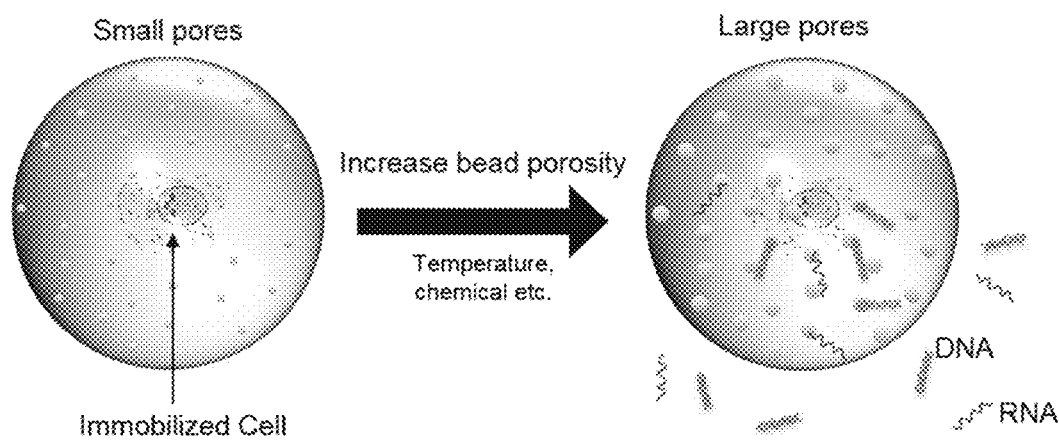
FIG. 3 is a schematic that illustrates an embodiment for increasing bead porosity by temperature or chemical means.

In some embodiments, pore size is increased sufficiently to retain the encapsulated cell, but to allow extracted nucleic acids to diffuse through the polymer shell, as depicted in FIG. 3. In some embodiments, the pore size of the contiguity particles can be controlled by altering the crosslinking chemistry. The final crosslinked pore size can further be altered by changing the environment of the contiguity particle, for example, by changing salt concentration, pH, or temperature, thereby allowing immobilized molecules to be released from the contiguity particle.

In some embodiments, the crosslinker is a reversible crosslinker. In some embodiments, a reversible crosslinker is capable of reversibly crosslinking the hydrogel polymer and is capable of being un-crosslinked in the presence of a cleaver. In some embodiments, a crosslinker can be cleaved by the presence of a reducing agent, by elevated temperature, or by an electric field. In some embodiments, the reversible crosslinker may be N,N'-bis(acryloyl)cystamine, a reversible crosslinker for polyacrylamide gels, wherein a disulfide linkage may be broken in the presence of a suitable reducing agent. As shown in FIG. 3, bead porosity may be increased by temperature or chemical means, thereby releasing contacting the crosslinker with a reducing agent cleaves the disulfide bonds of the crosslinker, breaking down the hollow beads. The hollow beads degrade, and release the contents, such as nucleic acids that were retained therein. In some embodiments, the crosslinker is cleaved by increasing the temperature to greater than 50, 55, 60, 65, 70, 75, 80, 85, 90, 95, or 100° C. In some embodiments, the crosslinker is cleaved by contacting the hollow beads with a reducing agent. In some embodiments, the reducing agents include phosphine compounds, water soluble phosphines, nitrogen containing phosphines and salts and derivatives thereof, dithioerythritol (DTE), dithiothreitol (DTT) (cis and trans isomers, respectively, of 2,3-dihydroxy-1,4-dithiolbutane), 2-mercaptoethanol or β-mercaptoethanol (BME), 2-mercaptoethanol or aminoethanethiol, glutathione, thioglycolate or thioglycolic acid, 2,3-dimercaptopropanol, tris(2-carboxyethyl)phosphine (TCEP), tris(hydroxymethyl)phosphine (THP), or P-[tris(hydroxymethyl)phosphine] propionic acid (THPP).

In some embodiments, elevating the temperature to increase diffusion or contacting with a reducing agent degrades the crosslinker, thereby releasing encapsulated genetic material from the contiguity particle.

In some embodiments, the crosslinking of the crosslinker establishes pores within the contiguity particle. In some embodiments, the size of the pores in the polymer shell are regulatable and are formulated to encapsulate cells or nucleic acids of greater than about 300 base pairs, but to allow smaller particles, such as reagents, or smaller sized nucleic acids of less than about 50 base pairs, such as primers, to pass through the pores. In some embodiments, the reagents including reagents for processing genetic material, such as reagents for isolating nucleic acids from a cell, for amplifying or sequencing nucleic acids, or for preparation of nucleic acid libraries. In some embodiments, reagents include, for example, lysozyme, proteinase K, random hexamers, polymerase (for example, Φ29 DNA polymerase, Taq polymerase, Bsu polymerase), transposase (for example, Tn5), primers (for example, P5 and P7 adaptor sequences), ligase, catalyzing enzyme, deoxynucleotide triphosphates, buffers, or divalent cations.

Exemplary cell types that can be used within a contiguity particle may include, for example, cells isolated from a tissue biopsy (e.g., from a tissue having a disease such as colon, breast, prostate, lung, skin cancer, or infected with a pathogen etc.) and normal cells from the same tissue, e.g., from the same patient; cells grown in tissue culture that are immortal (e.g., cells with a proliferative mutation or an immortalizing transgene), infected with a pathogen, or treated (e.g., with environmental or chemical agents such as peptides, hormones, altered temperature, growth condition, physical stress, cellular transformation, etc.), and normal cells (e.g., cells that are otherwise identical to the experimental cells except that they are not immortalized, infected, or treated, etc.); cells isolated from a mammal with a cancer, a disease, a geriatric mammal, or a mammal exposed to a condition, and cells from a mammal of the same species, e.g., from the same family, that is healthy or young; and differentiated cells and non-differentiated cells from the same mammal (e.g., one cell being the progenitor of the other in a mammal, for example). In one embodiment, cells of different types, e.g., neuronal and non-neuronal cells, or cells of different status (e.g., before and after a stimulus on the cells) may be compared. In another embodiment, the experimental material is cells susceptible to infection by a pathogen such as a virus, e.g., human immunodeficiency virus (HIV), etc., and the control material is cells resistant to infection by the pathogen. In another embodiment of the invention, the sample pair is represented by undifferentiated cells, e.g., stem cells, and differentiated cells. Cells from yeast, plants and animals, such as fish, birds, reptiles, amphibians and mammals may be used in the subject methods. In certain embodiments, mammalian cells, i.e., cells from mice, rabbits, primates, or humans, or cultured derivatives thereof, may be used.

Methods of Making Contiguity Particles

Some embodiments provided herein relate to methods of encapsulating a single cell within a polymer shell to form a contiguity particle. In some embodiments, a sample containing cells to be encapsulated within the contiguity particle is obtained. In some embodiments, the cells can be fixed with a fixative prior to encapsulation within the contiguity particle. As used herein, a fixative generally refers to an agent that can fix cells. For example, fixed cells can stabilize protein complexes, nucleic acid complexes, or protein-nucleic acid complexes in the cell. Suitable fixatives and cross-linkers can include, alcohol or aldehyde based fixatives, formaldehyde, glutaraldehyde, ethanol-based fixatives, methanol-based fixatives, acetone, acetic acid, osmium tetraoxide, potassium dichromate, chromic acid, potassium permanganate, mercurials, picrates, formalin, paraformaldehyde, amine-reactive NHS-ester crosslinkers such as bis[sulfosuccinimidyl] suberate (BS3), 3,3'-dithiobis [sulfosuccinimidylpropionate] (DTSSP), ethylene glycol bis [sulfosuccinimidylsuccinate] (sulfo-EGS), disuccinimidyl glutarate (DSG), dithiobis[succinimidyl propionate] (DSP), disuccinimidyl suberate (DSS), ethylene glycol bis[succinimidylsuccinate] (EGS), NHS-ester/diazirine crosslinkers such as NHS-diazirine, NHS-LC-diazirine, NHS—SS-diazirine, sulfo-NHS-diazirine, sulfo-NHS-LC-diazirine, and sulfo-NHS—SS-diazirine. In some embodiments, fixing a cell preserves the internal state of the cell thereby preventing modification of the cell during encapsulation of the cell within the contiguity particle.

Figure 4:
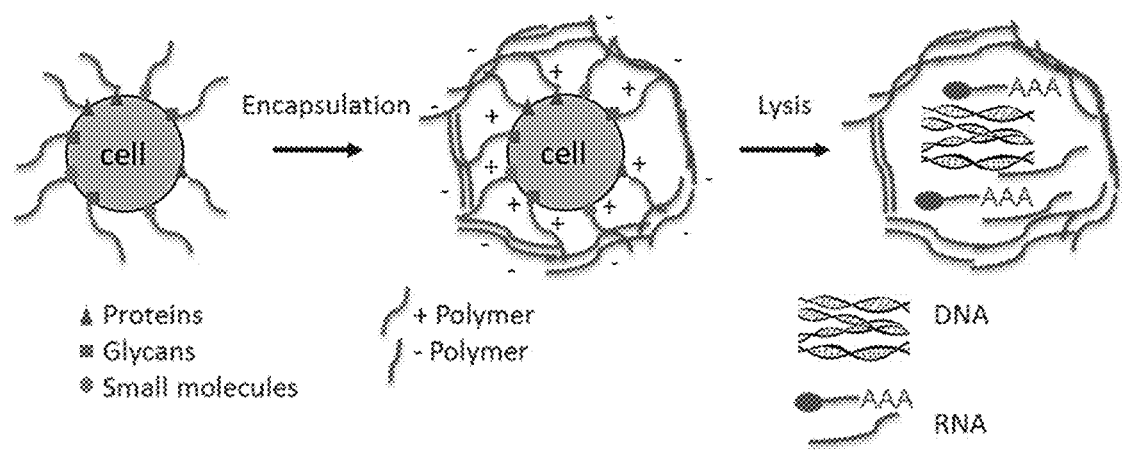
FIG. 4 is a schematic that illustrates an embodiment of a method of device-free cell encapsulation by depositing monomer units of a polymer over a single cell.
Figure 5:
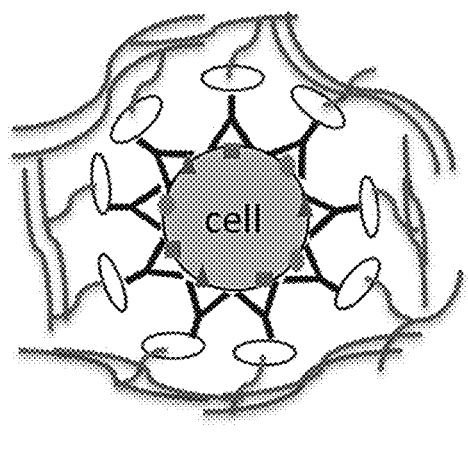
FIG. 5 is a schematic that illustrates an embodiment of an encapsulated cell within a polymer formed by device-free methods, wherein the polymer shell is attached to the cell through specific interactions with a specific binding molecule.

In some embodiments, a contiguity particle is prepared by static means, such as by single cell microwell/microarray methods or microdissection methods, without the need of a microfluidic device. Thus, in some embodiments, the contiguity particles described herein are prepared by a device-free method. Device-free methods may include initiation of polymerization on a cell surface by contacting the cell with a polymer, forming a polymer shell around the cell. Initiation of polymerization can occur by chemical reaction of active group on monomer units with specific moieties of membrane proteins, glycans or other small molecules. Initial step of monomer polymerization can be followed by one or several rounds of monomer units deposition promoted by either electrostatic or hydrophobic forces. Some of monomer layers can contain functional groups such as biotin or other ligands which can be used later for specific capture of encapsulated cells. For example, embedded cells can contain biotin and coating the embedded cells with magnetic streptavidin beads would make them magnetic allowing automated and easy processing, as shown in FIG. 4. Alternatively, live or fixed cell encapsulation can be initialized by light, or other physical or chemical means when initiator molecules are brought to cell surface either by passive adsorption, or in a targeted manner, for example attached to an antibody or other specific binding molecule and promote localized polymer amplification, as shown in FIG. 5.

Encapsulating cells in a targeted surface-initiated polymerization method enables the user to specifically select cells of interest and simultaneously prepares the cells for subsequent downstream assays, thereby combining flow sorting with single cell assays. Enrichment of specific cell types can be performed using cell separation kits utilizing magnetically labeled beads or custom binding molecules specific to certain cell membrane proteins conjugated to an enrichment surface.

In some embodiments, a contiguity particle is prepared by dynamic means, such as by vortex assisted emulsion, microfluidic droplet generation, or valve based microfluidics. As used herein, vortex assisted emulsion refers to vortexing a hydrogel polymer with a cell, including a fixed cell as described herein, in a container, such as in a tube, vial, or reaction vessel. The components can be mixed, for example by manual or mechanical vortexing or shaking. In some embodiments, manual mixing results in hollow beads that encapsulate genetic material having a size of 20, 25, 30, 35, 40, 45, 50, 55, 60, 65, 70, 75, 80, 85, 90, 95, 100, 110, 120, 130, 140, 150, 160, 170, 180, 190, or 200 µm in diameter, or a size within a range defined by any two of the aforementioned values. In some embodiments, the size of the beads is non-uniform, and thus, the size of the beads includes beads of various diameters.

In some embodiments, the contiguity particles are prepared by microfluidic flow techniques. Microfluidic flow includes use of a microfluidic device for assisted gel emulsion generation, as shown in FIG. 1. In some embodiments, the microfluidic device includes microchannels configured to produce a contiguity particle of a desired size and configured to encapsulate a single cell per contiguity particle. In some embodiments, the microfluidic device has a height of 50, 60, 70, 80, 90, 100, 110, 120, 130, 140, 150, 160, 170, 180, 190, or 200 µm, or a height within a range defined by any two of the aforementioned values. In some embodiments, the microfluidic device includes one or more channels. In some embodiments, the microfluidic device includes a channel for introducing a cell, including a fixed cell, that has been introduced to a polymer, a channel for introducing a crosslinker, and a channel for an immiscible fluid. In some embodiments, the width of the one or more channels is identical. In some embodiments, the width of the one or more channels is different. In some embodiments, the width of the one or more channels is 20, 30, 40, 45, 50, 55, 60, 65, 70, 75, 80, 85, 90, 95, 100, 105, 110, 115, 120, 125, 130, 135, 140, 145, or 150 µm, or a width within a range defined by any two of the aforementioned values. The width and height of the channel is not necessarily restricted to the values described herein and a person of skill in the art will recognize that the size of the contiguity particle will be dependent in part on the size of the channels of the microfluidic device. Thus, the size of the contiguity particle may be tuned in part by modifying the size of the channels. In addition to the size of the microfluidic device and the width of the channels, the flow rate of the channels may also affect the size of the contiguity particles, and may also effect the number of cells encapsulated within each contiguity particle.

In some embodiments, the flow rate of the cell in the polymer, including a fixed cell mixed with a polymer, through the microfluidic channel is 1, 2, 5, 10, 20, 30, 40, 50, 60, 70, 80, 90, 100, 110, 120, 130, 140, or 150 µL/min, or a rate within a range defined by any two of the aforementioned values. In some embodiments, the flow rate of the crosslinker in the microfluidic channel is 1, 2, 5, 10, 20, 30, 40, 50, 60, 70, 80, 90, 100, 110, 120, 130, 140, or 150 µL/min, or a rate within a range defined by any two of the aforementioned values. In some embodiments, the flow rate of the immiscible fluid in the microfluidic channel is 20, 30, 50, 80, 100, 150, 160, 170, 180, 190, 200, 225, 250, 275, 300, 325, 350, 375, or 400 µL/min, or a rate within a range defined by any two of the aforementioned values. In some embodiments, the cells mixed with the polymer, including fixed cells mixed with a polymer, and the crosslinker contact one another in the microfluidic droplet generator upstream of the immiscible fluid. The contiguity particles begin to form upon contact with the crosslinker, encapsulating cells within a polymer shell. The forming contiguity particles continue to flow through the microfluidic droplet generator into an immiscible fluid, such as a spacer oil and/or a crosslinking oil, at a flow rate less than the flow rate of the immiscible fluid, thereby forming droplets. In some embodiments, the immiscible fluid is introduced in two stages, as shown in FIG. 1, including as a spacer oil and as a crosslinker oil. In some embodiments, the spacer oil is a mineral oil, a hydrocarbon oil, a silicon oil, a fluorocarbon oil, or a polydimethylsiloxane oil, or mixtures thereof. The spacer oil as used herein is used to avoid crosslinking of the polymer at the channel aqueous-oil interphase.

In some embodiments, the contiguity particles are formed instantaneously by crosslinking with an instantaneous crosslinker. For example, cells encapsulated with a polymers like four-arm PEG maleimide or epoxide using a microfluidic droplet generator can be instantaneously crosslinked using crosslinkers that are dissolvable in oils such as mineral oil or fluorocarbon oils like HFE-7500, forming a crosslinking oil. In some embodiments, the crosslinking oil includes toluene, acetone, tetrahydrofuran with dithiol, amine functional groups as in the case of toluene 3,4 dithiol, 2,4 diaminotoluene, hexane dithiol, which readily diffuse into the forming droplets thereby instantaneously crosslinking the contiguity particles.

In some embodiments, the contiguity particles are formulated in a uniform size distribution. In some embodiments, the size of the contiguity particles is finely tuned by adjusting the size of the microfluidic device, the size of the one or more channels, or the flow rate through the microfluidic channels. In some embodiments, the resulting contiguity particle has a diameter ranging from 20 to 200 µm, for example, 20, 25, 30, 35, 40, 45, 50, 55, 60, 65, 70, 75, 80, 85, 90, 95, 100, 110, 120, 130, 140, 150, 160, 170, 180, 190, or 200 µm, or a diameter within a range defined by any two of the aforementioned values.

In some embodiments, the size and uniformity of the contiguity particles can be further controlled by contacting a hydrogel polymer prior to particle formation with a fluidic modifier, such as with an alcohol, including isopropyl alcohol. In the absence of isopropyl alcohol, contiguity particles form at a greater diameter than contiguity particles formed in the presence of isopropyl alcohol. Isopropyl alcohol influences the fluidic property of the hydrogel polymer, allowing modulation of the size of contiguity particles.

As will be recognized by those of skill in the art, the microfluidic device depicted in FIG. 1 is exemplary of a three channel microfluidic device, but the microfluidic device may be modified, varied, or altered to generate contiguity particles of a particular size or to generate contiguity particles formed from varied hydrogel materials or crosslinkers.

In some embodiments, a contiguity particle, whether prepared by vortex assisted emulsion or microfluidic inertial flow assisted emulsion, encapsulate a single cell, including a single fixed cell as described herein. In some embodiments, the number of cells within a contiguity particle can be controlled by diluting or concentration the solution containing the cell within the inputted sample. The sample including the cell is mixed with hydrogel polymer, and the hydrogel polymer containing the cells is submitted to vortex assisted emulsion or microfluidic flow assisted emulsion, as described herein.

In some embodiments, the contiguity particles are functionalized with a nucleotide. In some embodiments, the nucleotide is an oligonucleotide or polyT nucleotide. In some embodiments, the nucleotide is bound to the contiguity particles, and the functionalized contiguity particles can be used for targeted capture of a nucleotide of interest.

In some embodiments, the contiguity particles encapsulating a single cell are cured to sustain performing multiple co-assays on a single contiguity particle, including multiple buffer washes, multiple reagent exchanges, and multiple analyses based on the assay being performed. The formulated contiguity particles, prepared by any of the methods described herein, including surface-initiated polymerization techniques, vortexing, or by the microfluidic techniques may be loaded or seeded onto a patterned flow cell, a microarray, a plate with wells, an etched surface, a microfluidic channel, a bead, a column, or other surface for performing multiple co-assays on the encapsulated cell.

Methods of Performing Multiple Co-Assays on Cells Encapsulated within Contiguity Particles Some embodiments provided herein relate to methods of performing multiple sequential co-assays on a single cell encapsulated within a contiguity particle. In some embodiments, the method includes obtaining a contiguity particle as described herein and sequentially contacting the single cell encapsulated within the contiguity particle with reagents to perform multiple sequential co-assays.

In some embodiments, the contiguity particles are prepared as described herein, and contiguity particles are loaded onto a surface, such as a flow cell device, a well of a plate, a slide, or a patterned surface. In some embodiments, the surface is a flow cell device, and includes an insert having microwells or micropillars in an array for distribution of the contiguity particles for spatial indexing in a flow cell device. In some embodiments, the contiguity particles are loaded onto a welled plate with a single contiguity particle in each well. A welled plate may include, for example, a 12 well plate, a 24 well plate, a 48 well plate, a 96 well plate, a 384 well plate, a 1536 well plate, a 3456 well plate, or a 9600 well plate, or any number of wells in a plate, with a single contiguity particle, and thus a single cell, deposited into each well. In some embodiments, the contiguity particles are permeabilized with a permeabilization agent. In some embodiments, a permeabilization agent includes a mild detergent such as TritonX-100. In some embodiments, the permeabilization agent permeabilizes the cell membrane of the cell within the contiguity particle to increase accessibility to cellular nuclear acids, such as to genomic DNA and RNA. In some embodiments, the welled plate having a single contiguity particle deposited within each well is subjected to multiple co-assays in sequence, including, for example, buffer washes, lysis, DNA analysis, RNA analysis, protein analysis, tagmentation, nucleic acid amplification, nucleic acid sequencing, DNA library preparation, assay for transposase accessible chromatic using sequencing (ATAC-seq), contiguity-preserving transposition (CPT-seq), single cell combinatorial indexed sequencing (SCI-seq), or single cell genome amplification, or any combination thereof performed sequentially.

In some embodiments, the contiguity particle encapsulating a cell or viral particle is treated to purify and isolate nucleic acids from the cell. Thus, for example the contiguity particle is contacted with a lysis buffer. As used herein, "lysis" means perturbation or alteration to a cell wall or viral particle facilitating access to or release of the cellular RNA or DNA. Neither complete disruption nor breakage of the cell wall is an essential requirement for lysis. By the term "lysis buffer" is meant a buffer that contains at least one lysing agent. Typical enzymatic lysing agents include, but are not limited to, lysozyme, glucolase, zymolose, lyticase, proteinase K, proteinase E, and viral endolysins and exolysins. Thus, for example, lysis of cells in the contiguity particles may be performed by introducing lysing agents, such as lysozyme and proteinase K into the contiguity particles. The gDNA from the cells is now contained within the contiguity particles. In some embodiments, following lysis treatment, isolated nucleic acid is retained within the contiguity particle, and may be used for further processing.

DNA analysis refers to any technique used to amplify, sequence, or otherwise analyze DNA contained within the encapsulated cell. DNA amplification can be accomplished using PCR techniques or pyrosequencing. DNA analysis may also comprise non-targeted, non-PCR based DNA sequencing (e.g., metagenomics) techniques. As a non-limiting example, DNA analysis may include sequencing the hyper-variable region of the 16S rDNA (ribosomal DNA) and using the sequencing for species identification via DNA.

RNA analysis refers to any technique used to amplify, sequence, or otherwise analyze RNA contained within the encapsulated cell. The same techniques used to analyze DNA can be used to amplify and sequence RNA. RNA, which is less stable than DNA is the translation of DNA in response to a stimuli. Therefore, RNA analysis may provide a more accurate picture of the metabolically active members of the community and may be used to provide information about the community function of organisms in a sample. Nucleic acid sequencing refers to use of sequencing to determine the order of nucleotides in a sequence of a nucleic acid molecule, such as DNA or RNA.

The term "sequencing," as used herein, refers to a method by which the identity of at least 10 consecutive nucleotides (e.g., the identity of at least 20, at least 50, at least 100 or at least 200 or more consecutive nucleotides) of a polynucleotide is obtained.

The terms "next-generation sequencing" or "high-throughput sequencing" or "NGS" generally refers to high throughput sequencing technologies, including, but not limited to, massively parallel signature sequencing, high throughput sequencing, sequencing by ligation (e.g., SOLiD sequencing), proton ion semiconductor sequencing, DNA nanoball sequencing, single molecule sequencing, and nanopore sequencing and may refer to the parallelized sequencing-by-synthesis or sequencing-by-ligation platforms currently employed by Illumina, Life Technologies, or Roche, etc. Next-generation sequencing methods may also include nanopore sequencing methods or electronic-detection based methods such as Ion Torrent technology commercialized by Life Technologies or single molecule fluorescence-based method commercialized by Pacific Biosciences.

Protein analysis refers to the study of proteins in an encapsulated cell, and may include proteomic analysis, determination of post-translational modification of proteins of interest, determination of protein expression levels, or determination of protein interactions with other molecules, including with other proteins or with nucleic acids.

As used herein, the term "tagmentation" refers to the modification of DNA by a transposome complex comprising transposase enzyme complexed with adaptors comprising transposon end sequence. Tagmentation results in the simultaneous fragmentation of the DNA and ligation of the adaptors to the 5' ends of both strands of duplex fragments. Following a purification step to remove the transposase enzyme, additional sequences can be added to the ends of the adapted fragments, for example by PCR, ligation, or any other suitable methodology known to those of skill in the art.

Assay for transposase accessible chromatic using sequencing (ATAC-seq) refers to a rapid and sensitive method of integrative epigenomic analysis. ATAC-seq captures open chromatin sites and reveals interplay between genomic locations of open chromatin, DNA binding proteins, individual nucleosomes, and higher-order compaction at regulatory regions with nucleotide resolution. Classes of DNA binding factor that strictly avoid, can tolerate, or tend to overlap with nucleosomes have been discovered. Using ATAC-seq, the serial daily epigenomes of resting human T cells was measured and evaluated from a pro band via standard blood draws, demonstrating the feasibility of reading personal epigenomes in clinical timescales for monitoring health and disease. More specifically, ATAC-seq may be performed by treating chromatin from a single encapsulated cell within a contiguity particles with an insertional enzyme complex to produce tagged fragments of genomic DNA. In this step, the chromatin is tagmented (for example, fragmented and tagged in the same reaction) using an insertional enzyme such as Tn5 or MuA that cleaves the genomic DNA in open regions in the chromatin and adds adaptors to both ends of the fragments.

In some cases, the conditions may be adjusted to obtain a desirable level of insertion in the chromatin (e.g., an insertion that occurs, on average, every 50 to 200 base pairs in open regions). The chromatin used in the method may be made by any suitable method. In some embodiments, nuclei may be isolated, lysed, and the chromatin may be further purified, e.g., from the nuclear envelope. In other embodiments, the chromatin may be isolated by contacting isolated nuclei with the reaction buffer. In these embodiments, the isolated nuclei may lyse when it makes contact with the reaction buffer (which comprises insertional enzyme complexes and other necessary reagents), which allows the insertional enzyme complexes access to the chromatin. In these embodiments, the method may comprise isolating nuclei from a population of cells; and combining the isolated nuclei with the transposase and adaptors, wherein the combining results in both lysis of the nuclei to release said chromatin and production of the adaptor-tagged fragments of genomic DNA. The chromatin does not require cross-linking as in other methods (e.g., ChIP-SEQ methods).

After the chromatin has been fragmented and tagged to produce tagged fragments of genomic DNA, at least some of the adaptor tagged fragments are sequenced to produce a plurality of sequence reads. The fragments may be sequenced using any suitable method. For example, the fragments may be sequenced using Illumina's reversible terminator method, Roche's pyrosequencing method (454), Life Technologies' sequencing by ligation (the SOLiD platform) or Life Technologies' Ion Torrent platform. Examples of such methods are described in the following references: Margulies et al. (Nature 2005 437: 376-80); Ronaghi et al. (Analytical Biochemistry 1996 242: 84-9); Shendure et al. (Science 2005 309: 1728-32); Imelfort et al. (Brief Bioinform. 2009 10:609-18); Fox et al. (Methods Mol Biol. 2009; 553:79-108); Appleby et al. (Methods Mol Biol. 2009; 513:19-39) and Morozova et al. (Genomics. 2008 92:255-64), which are incorporated by reference herein for the general descriptions of the methods and the particular steps of the methods, including all starting products, methods for library preparation, reagents, and final products for each of the steps. As would be apparent, forward and reverse sequencing primer sites that are compatible with a selected next generation sequencing platform can be added to the ends of the fragments during the amplification step. In certain embodiments, the fragments may be amplified using PCR primers that hybridize to the tags that have been added to the fragments, where the primer used for PCR have 5' tails that are compatible with a particular sequencing platform. Methods of performing ATAC-seq are set forth in PCT Application No. PCT/US2014/038825, which is incorporated by reference herein in its entirety.

The term "chromatin," as used herein, refers to a complex of molecules including proteins and polynucleotides (e.g. DNA, RNA), as found in a nucleus of a eukaryotic cell. Chromatin is composed in part of histone proteins that form nucleosomes, genomic DNA, and other DNA binding proteins (e.g., transcription factors) that are generally bound to the genomic DNA.

Contiguity-preserving transposition sequencing (CPT-seq) refers to a method of sequencing while preserving contiguity information by the use of transposase to maintain the association of template nucleic acid fragments adjacent in the target nucleic acid. For example, CPT may be carried out on a nucleic acid, such as on DNA or RNA. The CPT-nucleic acid can be captured by hybridization of complimentary oligonucleotides having unique indexes or barcodes and immobilized on a solid support. In some embodiments, the oligonucleotide immobilized on the solid support may further comprise primer binding sites, unique molecular indices, in addition to barcodes. Advantageously, such use of transposomes to maintain physical proximity of fragmented nucleic acids increases the likelihood that fragmented nucleic acids from the same original molecule, e.g., chromosome, will receive the same unique barcode and index information from the oligonucleotides immobilized on a solid support. This will result in a contiguously-linked sequencing library with unique barcodes. The contiguously-linked sequencing library can be sequenced to derive contiguous sequence information. The contiguity particles described herein may be contacted with the CPT-seq reagents for performance of CPT-seq on nucleic acids extracted from the encapsulated cell.

As used herein the term "contiguity information" refers to a spatial relationship between two or more DNA fragments based on shared information. The shared aspect of the information can be with respect to adjacent, compartmental and distance spatial relationships. Information regarding these relationships in turn facilitates hierarchical assembly or mapping of sequence reads derived from the DNA fragments. This contiguity information improves the efficiency and accuracy of such assembly or mapping because traditional assembly or mapping methods used in association with conventional shotgun sequencing do not take into account the relative genomic origins or coordinates of the individual sequence reads as they relate to the spatial relationship between the two or more DNA fragments from which the individual sequence reads were derived.

Therefore, according to the embodiments described herein, methods of capturing contiguity information may be accomplished by short range contiguity methods to determine adjacent spatial relationships, mid-range contiguity methods to determine compartmental spatial relationships, or long range contiguity methods to determine distance spatial relationships. These methods facilitate the accuracy and quality of DNA sequence assembly or mapping, and may be used with any sequencing method, such as those described herein.

Contiguity information includes the relative genomic origins or coordinates of the individual sequence reads as they relate to the spatial relationship between the two or more DNA fragments from which the individual sequence reads were derived. In some embodiments, contiguity information includes sequence information from non-overlapping sequence reads.

In some embodiments, the contiguity information of a target nucleic acid sequence is indicative of haplotype information. In some embodiments, the contiguity information of a target nucleic acid sequence is indicative of genomic variants.

Single cell combinatorial indexed sequencing (SCI-seq) is a sequencing technique for simultaneously generating thousands of low-pass single cell libraries for somatic copy number variant detection.

Accordingly, multiple co-assays may be performed on a single cell for purposes of analyzing the cell or nucleic acids of the cell, including assays described herein, alone or in combination with any other assay.

The indexed contiguity particles can also be loaded directly onto the flow cells held through an array of posts/microwells. The indexed libraries released from the contiguity particles (chemical/temperature release) and bind to the flow cell. This allows a powered indexing approach where the first level of indexing comes from spatial location and then the next level comes from the indexed libraries from a single contiguity particle. Alternatively, indexed libraries extracted from the contiguity particles can be collectively loaded onto the flow cell.

In some embodiments, a cell encapsulated within a contiguity particle is contacted with one or more reagents for nucleic acid processing. In some embodiments, the cell is retained within the contiguity particle, and reagents are able to pass through the pores of the contiguity particle. In some embodiments, reagents can include lysis agents, nucleic acid purification agents, DNA amplification agents, tagmentation agents, PCR agents, or other agents used in processing of genetic materials. Thus, the contiguity particle provides a microenvironment for controlled reactions of cells, including nucleic acids extracted from the cells, within the contiguity particle by allowing a barrier for reagents to pass in and out of the polymer shell, while retaining the cell itself within the contiguity particle. In some embodiments, pores of the polymer shell are modulated to allow the flow of reagents and also the flow of nucleic acids, such as DNA and RNA extracted from the cell through the polymer shell.

In some embodiments, entire DNA library preparation can be accomplished seamlessly inside the contiguity particle with multiple reagent exchanges by passing through the porous hydrogel while retaining the gDNA and its library products within the polymer shell. The hydrogel may be resistant to high temperatures up to 95° C. for several hours to support different biochemical reactions.

As used herein, the terms "isolated," "to isolate," "isolation," "purified," "to purify," "purification," and grammatical equivalents thereof as used herein, unless specified otherwise, refer to the reduction in the amount of at least one contaminant (such as protein and/or nucleic acid sequence) from a sample or from a source (e.g., a cell) from which the material is isolated. Thus purification results in an "enrichment," for example, an increase in the amount of a desirable protein and/or nucleic acid sequence in the sample.

Following lysis and isolation of nucleic acids, amplification may be performed, such as multiple displacement amplification (MDA), which is a widely used technique for amplifying low quantities of DNA, especially from single cells. In some embodiments, the encapsulated nucleic acids are amplified, sequenced, or used for the preparation of nucleic acid libraries. As used herein, the terms "amplify" or "amplified" "amplifying" as used in reference to a nucleic acid or nucleic acid reactions, refer to in vitro methods of making copies of a particular nucleic acid, such as a target nucleic acid, or a nucleic acid encapsulated within a contiguity particle, for example, by an embodiment of the present invention. Numerous methods of amplifying nucleic acids are known in the art, and amplification reactions include polymerase chain reactions, ligase chain reactions, strand displacement amplification reactions, rolling circle amplification reactions, multiple annealing and looping based amplification cycles (MALBAC), transcription-mediated amplification methods such as NASBA, loop mediated amplification methods (e.g., "LAMP" amplification using loop-forming sequences. The nucleic acid that is amplified can be DNA comprising, consisting of, or derived from DNA or RNA or a mixture of DNA and RNA, including modified DNA and/or RNA. The products resulting from amplification of a nucleic acid molecule or molecules (for example, "amplification products"), whether the starting nucleic acid is DNA, RNA or both, can be either DNA or RNA, or a mixture of both DNA and RNA nucleosides or nucleotides, or they can comprise modified DNA or RNA nucleosides or nucleotides. A "copy" does not necessarily mean perfect sequence complementarity or identity to the target sequence. For example, copies can include nucleotide analogs such as deoxyinosine or deoxyuridine, intentional sequence alterations (such as sequence alterations introduced through a primer comprising a sequence that is hybridizable, but not complementary, to the target sequence, and/or sequence errors that occur during amplification.

The encapsulated nucleic acids that are isolated within the contiguity particle can be amplified according to any suitable amplification methodology known in the art. In some embodiments, the encapsulated nucleic acids are amplified within the contiguity particle. In some embodiments, the contiguity particle is captured on a solid support and degraded, wherein the encapsulated nucleic acids are released onto the solid support, and the nucleic acids are amplified on the solid support.

In some embodiments, the encapsulated nucleic acids are amplified within the contiguity particle. For example, in some embodiments, amplification primers and enzymes pass through the pores of the contiguity particle and hybridize to the encapsulated nucleic acids.

It will be appreciated that any of the amplification methodologies described herein or generally known in the art can be utilized with universal or target-specific primers to amplify encapsulated nucleic acids. Suitable methods for amplification include, but are not limited to, the polymerase chain reaction (PCR), strand displacement amplification (SDA), transcription mediated amplification (TMA) and nucleic acid sequence based amplification (NASBA), as described in U.S. Pat. No. 8,003,354, which is incorporated herein by reference in its entirety. The above amplification methods can be employed to amplify one or more nucleic acids of interest. For example, PCR, including multiplex PCR, SDA, TMA, NASBA and the like can be utilized to amplify encapsulated nucleic acids. In some embodiments, primers directed specifically to the nucleic acid of interest are included in the amplification reaction.

Other suitable methods for amplification of nucleic acids can include oligonucleotide extension and ligation, rolling circle amplification (RCA) (Lizardi et al., Nat. Genet. 19:225-232 (1998), which is incorporated herein by reference) and oligonucleotide ligation assay (OLA) technologies (See generally U.S. Pat. Nos. 7,582,420, 5,185,243, 5,679,524 and 5,573,907; EP 0 320 308 B1; EP 0 336 731 B1; EP 0 439 182 B1; WO 90/01069; WO 89/12696; and WO 89/09835, all of which are incorporated by reference). It will be appreciated that these amplification methodologies can be designed to amplify encapsulated nucleic acids. For example, in some embodiments, the amplification method can include ligation probe amplification or oligonucleotide ligation assay (OLA) reactions that contain primers directed specifically to the nucleic acid of interest. In some embodiments, the amplification method can include a primer extension-ligation reaction that contains primers directed specifically to the nucleic acid of interest, and which are capable of passing through the hydrogel pores. As a non-limiting example of primer extension and ligation primers that can be specifically designed to amplify a nucleic acid of interest, the amplification can include primers used for the Golden-Gate assay (Illumina, Inc., San Diego, Calif.) as exemplified by U.S. Pat. Nos. 7,582,420 and 7,611,869, each of which is incorporated herein by reference in its entirety. In each of the methods described, the reagents and components involved in the nucleic acid reaction are capable of passing through the pores of the contiguity particle while retaining the nucleic acid itself within the contiguity particle.

In some embodiments, the encapsulated nucleic acids are amplified using cluster amplification methodologies as exemplified by the disclosures of U.S. Pat. Nos. 7,985,565 and 7,115,400, the contents of each of which are incorporated herein by reference in their entirety. The incorporated materials of U.S. Pat. Nos. 7,985,565 and 7,115,400 describe methods of nucleic acid amplification which allow amplification products to be immobilized on a solid support in order to form arrays comprised of clusters or "colonies" of immobilized nucleic acid molecules. Each cluster or colony on such an array is formed from a plurality of identical immobilized polynucleotide strands and a plurality of identical immobilized complementary polynucleotide strands. The arrays so-formed are generally referred to herein as "clustered arrays". The products of solid-phase amplification reactions such as those described in U.S. Pat. Nos. 7,985,565 and 7,115,400 are so-called "bridged" structures formed by annealing of pairs of immobilized polynucleotide strands and immobilized complementary strands, both strands being immobilized on the solid support at the 5' end, preferably via a covalent attachment. Cluster amplification methodologies are examples of methods wherein an immobilized nucleic acid template is used to produce immobilized amplicons. Other suitable methodologies can also be used to produce immobilized amplicons from immobilized DNA fragments produced according to the methods provided herein. For example one or more clusters or colonies can be formed via solid-phase PCR whether one or both primers of each pair of amplification primers are immobilized. In some embodiments, the encapsulated nucleic acids are amplified within the contiguity particle, and then deposited in an array or on a solid support in a cluster.

Additional amplification methods include isothermal amplification. Exemplary isothermal amplification methods that can be used include, but are not limited to, multiple displacement amplification (MDA) as exemplified by, for example Dean et al., Proc. Natl. Acad. Sci. USA 99:5261-66 (2002) or isothermal strand displacement nucleic acid amplification exemplified by, for example U.S. Pat. No. 6,214,587, each of which is incorporated herein by reference in its entirety. Other non-PCR-based methods that can be used in the present disclosure include, for example, strand displacement amplification (SDA) which is described in, for example Walker et al., Molecular Methods for Virus Detection, Academic Press, Inc., 1995; U.S. Pat. Nos. 5,455,166, and 5,130,238, and Walker et al., Nucl. Acids Res. 20:1691-96 (1992) or hyperbranched strand displacement amplification which is described in, for example Lage et al., Genome Research 13:294-307 (2003), each of which is incorporated herein by reference in its entirety. Isothermal amplification methods can be used with the strand-displacing Phi 29 polymerase or Bst DNA polymerase large fragment, 5'→3' exo— for random primer amplification of genomic DNA. The use of these polymerases takes advantage of their high processivity and strand displacing activity. High processivity allows the polymerases to produce fragments that are 10-20 kb in length. As set forth above, smaller fragments can be produced under isothermal conditions using polymerases having low processivity and strand-displacing activity such as Klenow polymerase. Additional description of amplification reactions, conditions and components are set forth in detail in the disclosure of U.S. Pat. No. 7,670,810, which is incorporated herein by reference in its entirety. In some embodiments, the polymerases, reagents, and components required to perform these amplification reactions are capable of passing through the pores of the contiguity particles to interact with the encapsulated nucleic acids, thereby amplifying the nucleic acids within the contiguity particles. In some embodiments, random hexamers are annealed to the denatured DNA followed by strand displacement synthesis at a constant temperature in the presence of a catalyzing enzyme, Phi 29. This results in DNA amplification within the contiguity particles as confirmed by an increase in the fluorescence intensity (DNA was stained with SYTOX) after MDA. Independently, Nextera based tagmentation after lysis and clean up and subsequent gDNA amplification via PCR as indicated by a substantial increase in fluorescence intensity within the contiguity particles after Nextera tagmentation and PCR may also be performed. After this Nextera library preparation, the contiguity particles may be heated to 80° C. for 3 minutes to release the contents of the contiguity particles namely, the sequencing ready library products from a cell.

Another nucleic acid amplification method that is useful in the present disclosure is Tagged PCR which uses a population of two-domain primers having a constant 5' region followed by a random 3' region as described, for example, in Grothues et al. Nucleic Acids Res. 21(5):1321-2 (1993), incorporated herein by reference in its entirety. The first rounds of amplification are carried out to allow a multitude of initiations on heat denatured DNA based on individual hybridization from the randomly-synthesized 3' region. Due to the nature of the 3' region, the sites of initiation are contemplated to be random throughout the genome. Thereafter, the unbound primers can be removed and further replication can take place using primers complementary to the constant 5' region.

In some embodiments, the encapsulated nucleic acids are sequenced in full or in part within the contiguity particles. The encapsulated nucleic acids can be sequenced according to any suitable sequencing methodology, such as direct sequencing, including sequencing by synthesis, sequencing by ligation, sequencing by hybridization, nanopore sequencing and the like.

One sequencing methodology is sequencing-by-synthesis (SBS). In SBS, extension of a nucleic acid primer along a nucleic acid template (e.g. a target nucleic acid or amplicon thereof) is monitored to determine the sequence of nucleotides in the template. The underlying chemical process can be polymerization (e.g. as catalyzed by a polymerase enzyme). In a particular polymerase-based SBS embodiment, fluorescently labeled nucleotides are added to a primer (thereby extending the primer) in a template dependent fashion such that detection of the order and type of nucleotides added to the primer can be used to determine the sequence of the template.

One or more amplified encapsulated nucleic acids can be subjected to an SBS or other detection technique that involves repeated delivery of reagents in cycles. For example, to initiate a first SBS cycle, one or more labeled nucleotides, DNA polymerase, etc., can be flowed into/ through a contiguity particle that houses one or more amplified nucleic acid molecules. Those sites where primer extension causes a labeled nucleotide to be incorporated can be detected. Optionally, the nucleotides can further include a reversible termination property that terminates further primer extension once a nucleotide has been added to a primer. For example, a nucleotide analog having a reversible terminator moiety can be added to a primer such that subsequent extension cannot occur until a deblocking agent is delivered to remove the moiety. Thus, for embodiments that use reversible termination, a deblocking reagent can be delivered to the flow cell (before or after detection occurs). Washes can be carried out between the various delivery steps. The cycle can then be repeated n times to extend the primer by n nucleotides, thereby detecting a sequence of length n. Exemplary SBS procedures, fluidic systems and detection platforms that can be readily adapted for use with amplicons produced by the methods of the present disclosure are described, for example, in Bentley et al., Nature 456:53-59 (2008), WO 04/018497; U.S. Pat. No. 7,057,026; WO 91/06678; WO 07/123744; U.S. Pat. Nos. 7,329,492; 7,211,414; 7,315,019; 7,405,281, and US 2008/0108082, each of which is incorporated herein by reference.

Other sequencing procedures that use cyclic reactions can be used, such as pyrosequencing. Pyrosequencing detects the release of inorganic pyrophosphate (PPi) as particular nucleotides are incorporated into a nascent nucleic acid strand (Ronaghi, et al., Analytical Biochemistry 242(1), 84-9 (1996); Ronaghi, Genome Res. 11(1), 3-11 (2001); Ronaghi et al. Science 281(5375), 363 (1998); U.S. Pat. Nos. 6,210, 891; 6,258,568 and 6,274,320, each of which is incorporated herein by reference). In pyrosequencing, released PPi can be detected by being immediately converted to adenosine triphosphate (ATP) by ATP sulfurylase, and the level of ATP generated can be detected via luciferase-produced photons. Thus, the sequencing reaction can be monitored via a luminescence detection system. Excitation radiation sources used for fluorescence based detection systems are not necessary for pyrosequencing procedures. Useful fluidic systems, detectors and procedures that can be adapted for application of pyrosequencing to amplicons produced according to the present disclosure are described, for example, in WIPO Pat. App. Ser. No. PCT/US11/57111, US 2005/0191698 A1, U.S. Pat. Nos. 7,595,883, and 7,244,559, each of which is incorporated herein by reference.

Some embodiments can utilize methods involving the real-time monitoring of DNA polymerase activity. For example, nucleotide incorporations can be detected through fluorescence resonance energy transfer (FRET) interactions between a fluorophore-bearing polymerase and γ-phosphate-labeled nucleotides, or with zero mode waveguides (ZMWs). Techniques and reagents for FRET-based sequencing are described, for example, in Levene et al. Science 299, 682-686 (2003); Lundquist et al. Opt. Lett. 33, 1026-1028 (2008); Korlach et al. Proc. Natl. Acad. Sci. USA 105, 1176-1181 (2008), the disclosures of which are incorporated herein by reference.

Some SBS embodiments include detection of a proton released upon incorporation of a nucleotide into an extension product. For example, sequencing based on detection of released protons can use an electrical detector and associated techniques that are commercially available. Examples of such sequencing systems are pyrosequencing (e.g. commercially available platform from 454 Life Sciences a subsidiary of Roche), sequencing using γ-phosphate-labeled nucleotides (e.g. commercially available platform from Pacific Biosciences) and sequencing using proton detection (e.g. commercially available platform from Ion Torrent subsidiary of Life Technologies) or sequencing methods and systems described in US 2009/0026082 A1; US 2009/ 0127589 A1; US 2010/0137143 A1; or US 2010/0282617 A1, each of which is incorporated herein by reference. Methods set forth herein for amplifying target nucleic acids using kinetic exclusion can be readily applied to substrates used for detecting protons. More specifically, methods set forth herein can be used to produce clonal populations of amplicons that are used to detect protons.

Another sequencing technique is nanopore sequencing (see, for example, Deamer et al. Trends Biotechnol. 18, 147-151 (2000); Deamer et al. Acc. Chem. Res. 35:817-825 (2002); Li et al. Nat. Mater. 2:611-615 (2003), the disclosures of which are incorporated herein by reference). In some nanopore embodiments, the target nucleic acid or individual nucleotides removed from a target nucleic acid pass through a nanopore. As the nucleic acid or nucleotide passes through the nanopore, each nucleotide type can be identified by measuring fluctuations in the electrical conductance of the pore. (U.S. Pat. No. 7,001,792; Soni et al. Clin. Chem. 53, 1996-2001 (2007); Healy, Nanomed. 2, 459-481 (2007); Cockroft et al. J. Am. Chem. Soc. 130, 818-820 (2008), the disclosures of which are incorporated herein by reference).

Exemplary methods for array-based expression and genotyping analysis that can be applied to detection according to the present disclosure are described in U.S. Pat. No. 7,582, 420; 6,890,741; 6,913,884 or 6,355,431 or US Pat. Pub. Nos. 2005/0053980 A1; 2009/0186349 A1 or US 2005/0181440 A1, each of which is incorporated herein by reference.

In the methods of isolating nucleic acids, amplification, and sequencing as described herein, various reagents are used for nucleic acid isolation and preparation. Such reagents may include, for example, lysozyme, proteinase K, random hexamers, polymerase (for example, Φ29 DNA polymerase, Taq polymerase, Bsu polymerase), transposase (for example, Tn5), primers (for example, P5 and P7 adaptor sequences), ligase, catalyzing enzyme, deoxynucleotide triphosphates, buffers, or divalent cations. These reagents pass through the pores of the contiguity particles, whereas the genetic material is retained within the contiguity particles. An advantage of the methods set forth herein is that they provide for an encapsulated microenvironment for the processing of nucleic acids within a contiguity particle. This enables single cell processing for rapid and efficient processing of a target nucleic acid.

Adaptors can include sequencing primer sites, amplification primer sites, and indexes. As used herein an "index" can include a sequence of nucleotides that can be used as a molecular identifier and/or barcode to tag a nucleic acid, and/or to identify the source of a nucleic acid. In some embodiments, an index can be used to identify a single nucleic acid, or a subpopulation of nucleic acids. In some embodiments, nucleic acid libraries can be prepared within a contiguity particle. In some embodiments, a single cell encapsulated within a contiguity particle may be used for combinatorial indexing of the single cell, for example, using a contiguity preserving transposition (CPT-seq) approach. In some embodiments, DNA from a single cell may be barcoded by encapsulation of single cell after WGA amplification with another contiguity particle carrying barcoded transposons and dissolving the gel matrix by contacting it with a reducing agent, for example, to release genomic DNA for barcoding.

Embodiments of the "spatial indexing" methods and techniques described herein shortens data analysis and simplifies the process of library preparation from single cells and long DNA molecules. Existing protocols for single cell sequencing requires efficient physical separation of the cells and uniquely barcoding each isolated cell and pooling everything back together to do sequencing. Current protocols for synthetic long reads also requires cumbersome barcoding steps, and pooling each barcoded fragments together for sequencing and letting data analysis to distinguish genetic information coming from each barcoded cell. During these long processes there is also loss of genetic material which causes dropouts in the sequences. Embodiments described herein not only shorten the process but also increase data resolution for single cells. Furthermore, embodiments provided herein simplify the assembly of genomes of new organisms. Embodiments described herein may be used to reveal rare genetic variations and co-occurrence of mutations. In some embodiments, DNA library confined in the contiguity particles until release provide the opportunity to control the size of the fragments that is released on the surface by controlling the release process and hydrogel formulation.

In some embodiments, the library may be amplified using primer sites in the adaptor sequences, and sequenced using sequencing primer sites in the adaptor sequences. In some embodiments the adaptor sequences can include indexes to identify the source of the nucleic acids. The efficiency of subsequent amplification steps can be reduced by the formation of primer-dimers. To increase the efficiency of subsequent amplification steps, non-ligated single-stranded adaptors can be removed from ligation products.

Preparing Nucleic Acid Libraries with Contiguity Particles

Some embodiments of the systems, methods and compositions provided herein include methods in which adaptors are ligated to target nucleic acids. Adaptors can include sequencing primer binding sites, amplification primer binding sites, and indexes. For example, an adaptor can include a P5 sequence, a P7 sequence, or a complement thereof. As used herein a P5 sequence comprises a sequence defined by SEQ ID NO: 1 (AATGATACGGCGACCACCGA) and a P7 sequence comprises a sequence defined by SEQ ID NO: 2 (CAAGCAGAAGACGGCATACGA). In some embodiments, the P5 or P7 sequence can further include a spacer polynucleotide, which may be from 1 to 20, such as 1 to 15, or 1 to 10, nucleotides, such as 2, 3, 4, 5, 6, 7, 8, 9, or 10 nucleotides in length. In some embodiments, the spacer includes 10 nucleotides. In some embodiments, the spacer is a polyT spacer, such as a 10T spacer. Spacer nucleotides may be included at the 5' ends of polynucleotides, which may be attached to a suitable support via a linkage with the 5' end of the polynucleotide. Attachment can be achieved through a sulphur-containing nucleophile, such as phosphorothioate, present at the 5' end of the polynucleotide. In some embodiments, the polynucleotide will include a polyT spacer and a 5' phosphorothioate group. Thus, in some embodiments, the P5 sequence is 5' phosphorothioate-TTTTTTTTTTAATGATACGGCGACCACCGA-3 (SEQ ID NO: 3), and in some embodiments, the P7 sequence is 5' phosphorothioate-TTTTTTTTTT CAAGCAGAAGACGG-CATACGA-3' (SEQ ID NO: 4).

Indexes can be useful to identify the source of a nucleic acid molecule. In some embodiments, an adaptor can be modified to prevent the formation of concatemers, for example by the addition of blocking groups that prevent extension of the adaptor at one or both ends. Examples of 3' blocking groups include a 3'-spacer C3, a dideoxynucleotide, and attachment to a substrate. Examples of 5' blocking groups include a dephosphorylated 5' nucleotide, and attachment to a substrate.

Adaptors include nucleic acids, such as single-stranded nucleic acids. Adaptors can include short nucleic acids having a length less than, greater than, or equal to about 5 nucleotides, 10 nucleotides, 20 nucleotides, 30 nucleotides, 40 nucleotides, 50 nucleotides, 60 nucleotides, 70 nucleotides, 80 nucleotides, 90 nucleotides, 100 nucleotides, or a range between any two of the foregoing sizes. In some embodiments, the adaptors are of sufficient size to pass through the pores of the contiguity particles. Target nucleic acids include DNA, such as genomic or cDNA; RNA, such as mRNA, sRNA or rRNA; or a hybrid of DNA and RNA. The nucleic acid can be isolated from a single cell encapsulated within a contiguity particle. A nucleic acid can contain phosphodiester bonds, and can include other types of backbones, comprising, for example, phosphoramide, phosphorothioate, phosphorodithioate, O-methylphosphoroamidite and peptide nucleic acid backbones and linkages. A nucleic acid can contain any combination of deoxyribo- and ribonucleotides, and any combination of bases, including uracil, adenine, thymine, cytosine, guanine, inosine, xanthanine, hypoxanthanine, isocytosine, isoguanine, and base analogs such as nitropyrrole (including 3-nitropyrrole) and nitroindole (including 5-nitroindole). In some embodiments, a nucleic acid can include at least one promiscuous base. A promiscuous base can base-pair with more than one different type of base and can be useful, for example, when included in oligonucleotide primers or inserts that are used for random hybridization in complex nucleic acid samples such as genomic DNA samples. An example of a promiscuous base includes inosine that may pair with adenine, thymine, or cytosine. Other examples include hypoxanthine, 5-nitroindole, acylic 5-nitroindole, 4-nitropyrazole, 4-nitroimidazole and 3-nitropyrrole. Promiscuous bases that can base-pair with at least two, three, four or more types of bases can be used.

Target nucleic acids can include a sample in which the average size of a nucleic acid in the sample is less than, greater than, or equal to about 2 kb, 1 kb, 500 bp, 400 bp, 200 bp, 100 bp, 50 bp, or a range between any two of the foregoing sizes. In some embodiments, the average size of a nucleic acid in the sample is less than, greater than, or equal to about 2000 nucleotides, 1000 nucleotides, 500 nucleotides, 400 nucleotides, 200 nucleotides, 100 nucleotides, 50 nucleotides, or a range between any two of the foregoing sizes. In some embodiments, the nucleic acid is of sufficient size that the nucleic acid is entrapped within the contiguity particle such that it cannot pass through the pores of the contiguity particle.

An example method includes dephosphorylating the 5' ends of target nucleic acids to prevent the formation of concatemers in subsequent ligation steps; ligating first adaptors to the 3' ends of the dephosphorylated targets using a ligase, in which the 3' ends of the first adaptors are blocked; re-phosphorylating of the 5' ends of the ligated targets; ligating a second adaptor to the 5' ends of the dephosphorylated targets using the single-stranded ligase, in which the 5' ends of the second adaptors are non-phosphorylated.

Another example includes partial digestion of the nucleic acid with a 5' exonuclease to form a double-stranded nucleic acid with single-stranded 3' overhangs. An adaptor containing a 3' blocking group can be ligated to the 3' ends of double-stranded nucleic acid with 3' overhangs. The double-stranded nucleic acid with 3' overhangs with ligated adaptors can be dehybridized to form single-stranded nucleic acids. An adaptor containing a non-phosphorylated 5' end can be ligated to the 5' end of the single-stranded nucleic acid.

Methods to dephosphorylate nucleic acids, such as the 5' nucleotide of a nucleic acid include contacting a nucleic acid with a phosphatase. Examples of phosphatases include calf intestinal phosphatase, shrimp alkaline phosphatase, Antarctic phosphatase, and APEX alkaline phosphatase (Epicentre).

Methods to ligate nucleic acids include contacting nucleic acids with a ligase. Examples of ligases include T4 RNA ligase 1, T4 RNA ligase 2, RtcB ligase, Methanobacterium RNA ligase, and TS2126 RNA ligase (CIRCLIGASE).

Methods to phosphorylate nucleic acids, such as the 5' nucleotide of a nucleic acid include contacting a nucleic acid with a kinase. Examples of kinases include T4 polynucleotide kinase.

Embodiments provided herein relate to preparing nucleic acids libraries in a contiguity particle, such that the nucleic acid library is prepared in a single reaction volume.

Embodiments of the systems and methods provided herein include kits, containing any one or more of the hydrogel polymers, crosslinkers, or microfluidic devices for preparing contiguity particles that encapsulate a cell, and further including components useful for processing of the genetic material, including reagents for cell lysis, and nucleic acid amplification and sequencing, or for nucleic acid library preparation, including lysozyme, proteinase K, random hexamers, polymerase (for example, Φ29 DNA polymerase, Taq polymerase, Bsu polymerase), transposase (for example, Tn5), primers (for example, P5 and P7 adaptor sequences), ligase, catalyzing enzyme, deoxynucleotide triphosphates, buffers, or divalent cations as described herein, and as used for the respective processing of genetic material.

EXAMPLES

Example 1—Preparation of Contiguity Particles

The following example demonstrates an embodiment of preparing contiguity particles encapsulating a single cell using a microfluidic droplet generator.

Samples containing cells stored at −80° C. were thawed at room temperature. 100 µL of each sample was transferred to a sterile 1.7 mL tube, and the sample was washed once with 1 mL 0.85% NaCl. The sample was pelleted and wash solution was removed. The cell pellet was mixed with a hydrogel solution to resuspend the cells in the hydrogel solution.

Figure 6:
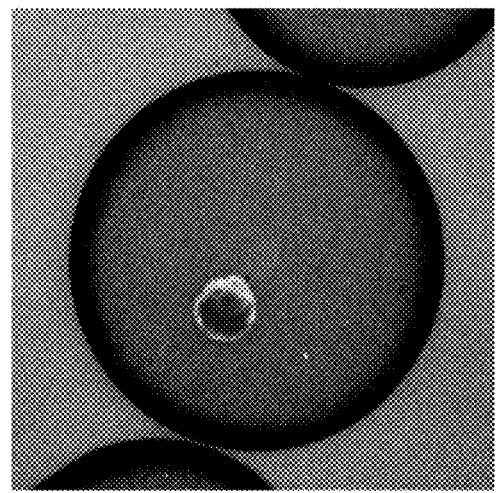
FIG. 6 depicts micrograph images of beads stained with fluorescent dyes, depicting cells encapsulated within the beads. The micrograph images depict (from left to right): staining with thiol-specific fluorophores, targeting free PEG-maleimide; staining with Texas Red fluorophores targeting free —SH groups; and nuclei staining with Hoechst staining.
Figure 6:
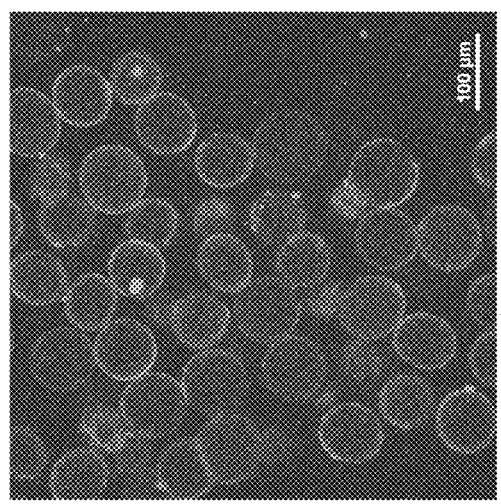
Figure 6:
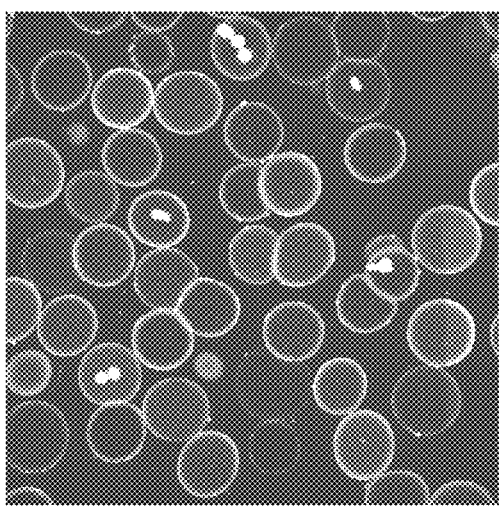

To generate contiguity particles of a uniform size distribution, microfluidic droplet generators were used, such as the generator illustrated in FIG. 1. The solution containing a hydrogel polymer and a cell was introduced into a first channel of the microfluidic droplet generator. Mineral oil, used as a spacer oil, was added to a second channel, and a crosslinker was added to a third channel. Upon contacting the crosslinker in the third channel, the hydrogel instantaneously formed contiguity particles encapsulating a single cell. As depicted in FIG. 6, contiguity particles were stained with a fluorescent dye that targets the —SH groups of the polymer shell of the contiguity particles. The right panel of FIG. 6 shows staining of a single cell within a contiguity particle, depicting a 60× objective image of a contiguity particle stained with Hoechst (blue-nuclear stain) and AF-647 BSA that diffuses into the contiguity particle through the polymer shell pores. The type of crosslinking oil was selected to tune the rapidity of crosslinking, including a slow crosslinker or an instantaneous crosslinker, as shown in Table 1:

TABLE 1

Crosslinking Chemistries

| Contiguity Particle Type | Crosslinkers | Cross-linking Time | Size Homogeneity | Bead Curing |
|---|---|---|---|---|
| Slow Cross-linker | PEG-epoxide + Peg-amine<br>PEG-dithiol + PEG-acrylate | >12 hours<br>4 hours | Good<br>Average | Complete<br>In-complete |
| Instan-taneous | Dithiol Oil + PEG-maleimide | Instan-taneous | Good | Complete |
| Cross-linker | PEG epoxide + amine oil | Instan-taneous | Good | Complete |

Example 2—Co-Assays Performed on Contiguity Particles

The following example demonstrates exemplary assays performed on contiguity particles from Example 1, including SCI-seq, ATAC-seq, combinatorial indexing, and single cell whole genome amplification.

Contiguity particles from Example 1 were obtained and deposited onto a plate having wells, such that a single contiguity particle was deposited into a single well. Cells were lysed by introducing a lysis buffer, following by wash, thereby extracting nucleic acids from the cells. The contiguity particles with the lysed cells were then exposed to a series of assays as described below.

Figure 7:
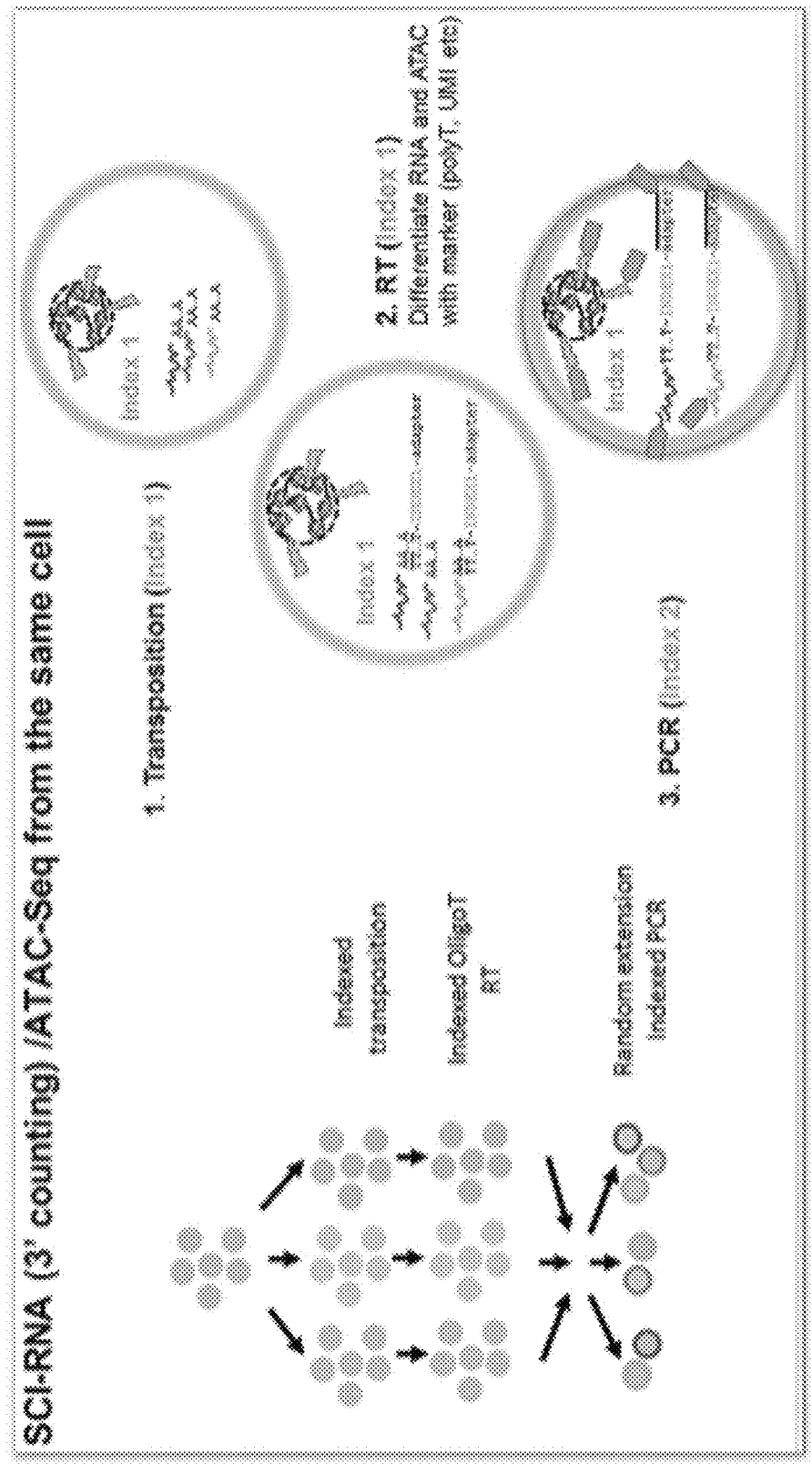
FIG. 7 is a schematic that illustrates an embodiment of a method of performing multiple co-assays on a hollow bead encapsulating a cell.

As outlined in FIG. 7, indexed transposomes (TSM) were used to tagment genomic DNA, generating ATAC-seq fragments. After proteinase/SDS treatment, the oligoT with the same index as TSM was added to each well to initiate cDNA synthesis by reverse transcription (RT). The PCR adapter on the other end was introduced by randomer extension. This generated Index 1. Contiguity particles from each well were pooled together then split into an indexed PCR plate to generate Index 2. This 2-tier indexing can be scaled up to 150,000 (384×384) cells; The final library generated was a mixture of ATAC-seq and RNA-seq, in which the gDNA and cDNA from the same cell was grouped by the same index, and the oligoT-UMI pattern served as an internal marker to distinguish RNA signal from ATAC signal.

Figure 8:
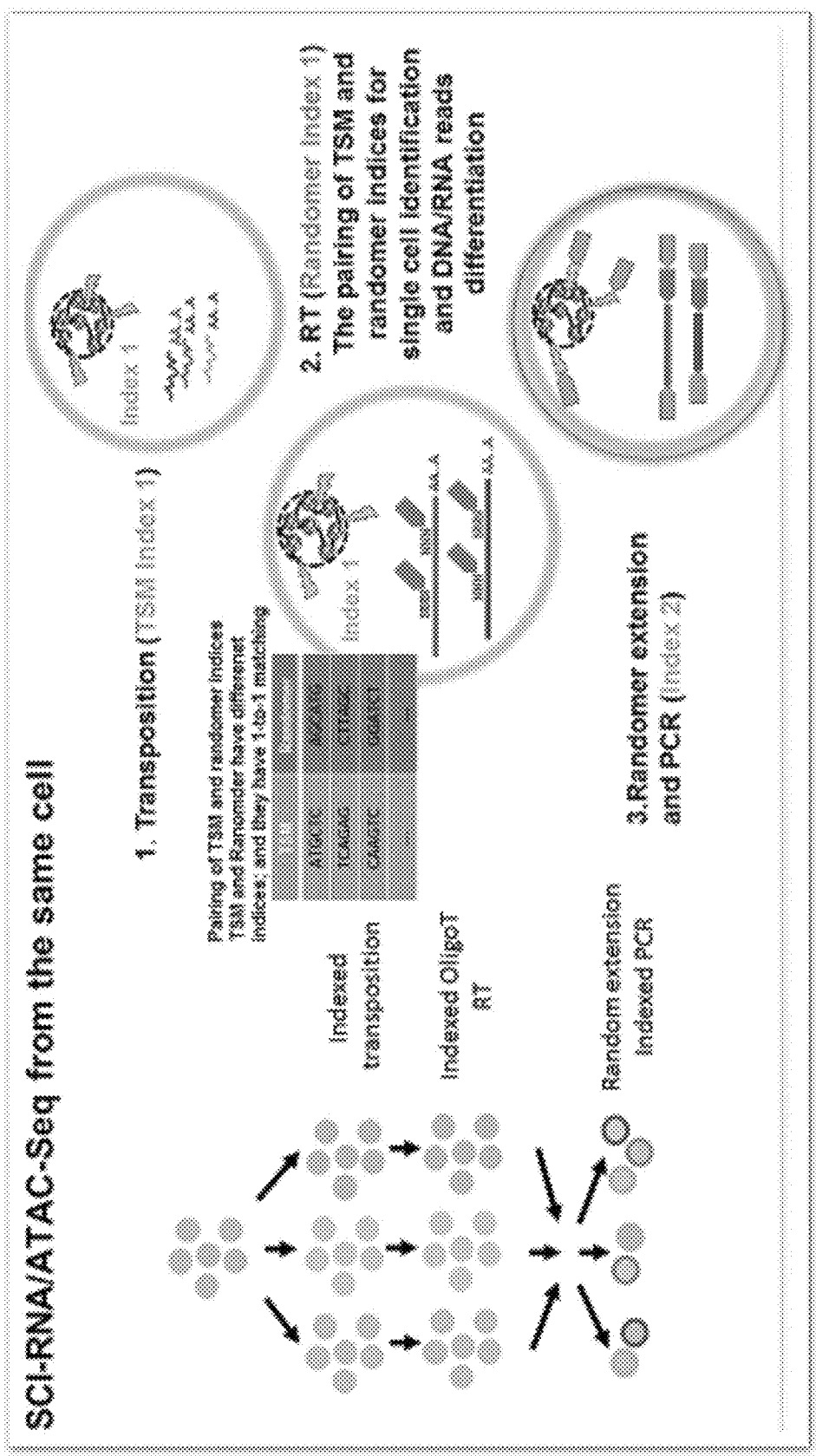
FIG. 8 is a schematic that illustrates an embodiment of a method of performing multiple co-assays on a hollow bead encapsulating a cell.

In addition, random extension was also used for full length RNA-seq, as shown in FIG. 8. In this case the indices of TSM were different from the indices of the randomers. The 1-to-1 matching between these 2 indices set helped identify the reads from a single cell and differentiated DNA and RNA signals. UMI was also applied in this method to improve the accuracy of reads analysis.

Figure 9:
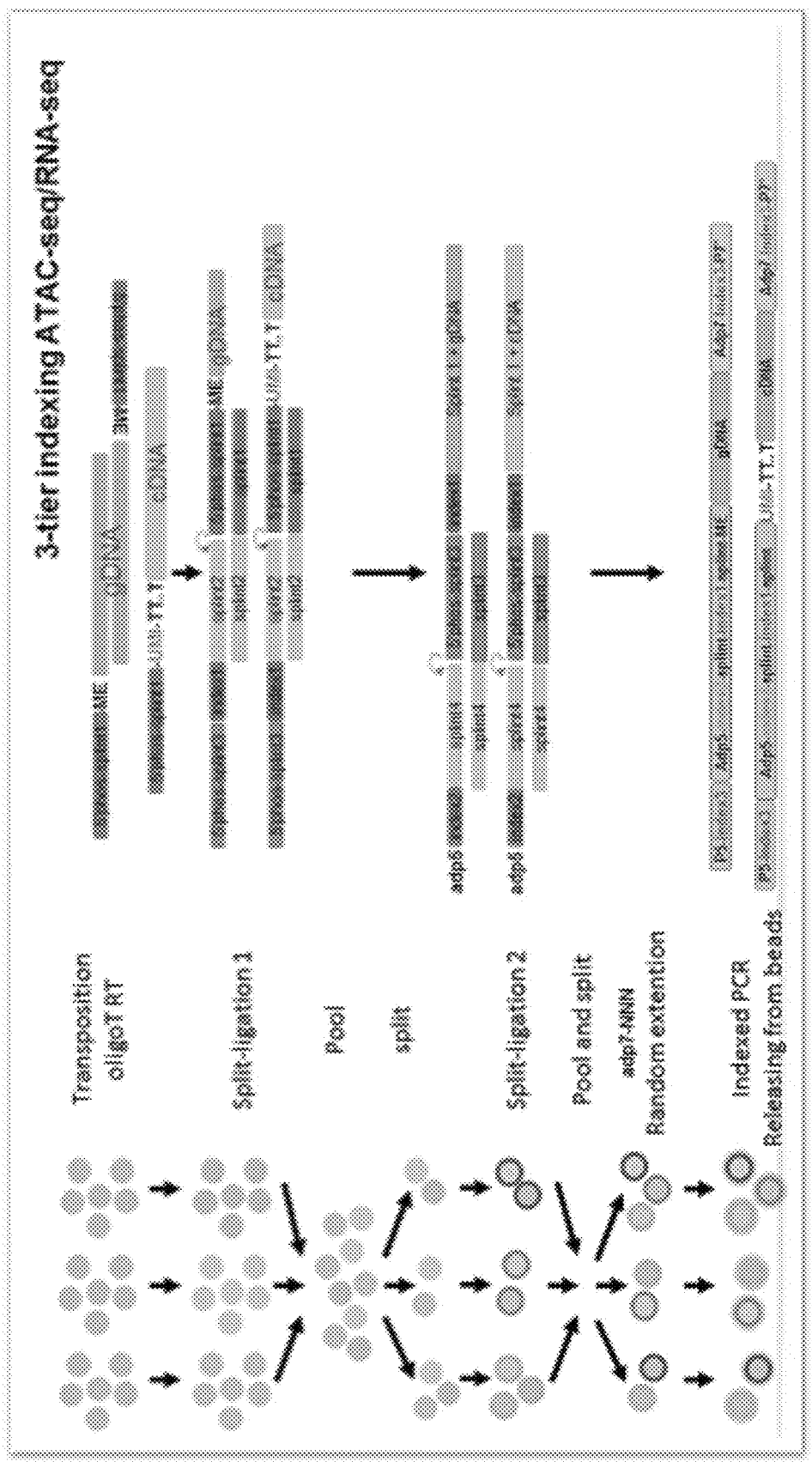
FIG. 9 is a schematic that illustrates an embodiment of a method of performing multiple co-assays on a hollow bead encapsulating a cell.
Figure 10:
FIG. 10 is a schematic that illustrates an embodiment of a method of performing multiple co-assays on a hollow bead encapsulating a cell.

A 3-tiered combinatorial indexing assay was also performed using two rounds of indexed splint-ligation and one round of indexed PCR, as outlined in the schematic of FIG. 9. In this method, TSM and oligoT are universal, both containing a splint1 fragment, which enabled the index addition by splint-ligation. Three-tier indexing achieved up to 1 million cell throughput (96×96×96). Another 3-tier combinatorial indexing for ATAC-seq was performed using indexed TSMs to increase cell throughput, as outlined in FIG. 10. Rather than using a universal TSM, TSMs contained a unique index on its B7G and A7G side. Two different splints were used to attach indexed adapters required for indexed PCR. In FIG. 10, the indexing included the following components: B15 adaptor sequence (SEQ ID NO: 5), N6, and Link1, together forming a B15_N6_Link1 sequence (SEQ ID NO: 11); a Phos_Link2, A7G sequence (SEQ ID NO: 9), and ME sequence (SEQ ID NO: 7), together forming a Phos_Link2_A7G_ME sequence (SEQ ID NO: 12); an A14 adaptor sequence (SEQ ID NO: 6), N6, and Link1, together forming an A14_N6_Link1 sequence (SEQ ID NO: 13); and a Phos_Link2, B7G (SEQ ID NO: 10), and ME sequence (SEQ ID NO: 7), together forming a Phos_Link2_B7G_ME sequence (SEQ ID NO: 14). FIG. 10 also provides an ME complementary sequence (SEQ ID NO: 8), a Splint 1 sequence (SEQ ID NO: 15), and a Splint 2 sequence (SEQ ID NO: 16).

Figure 11:
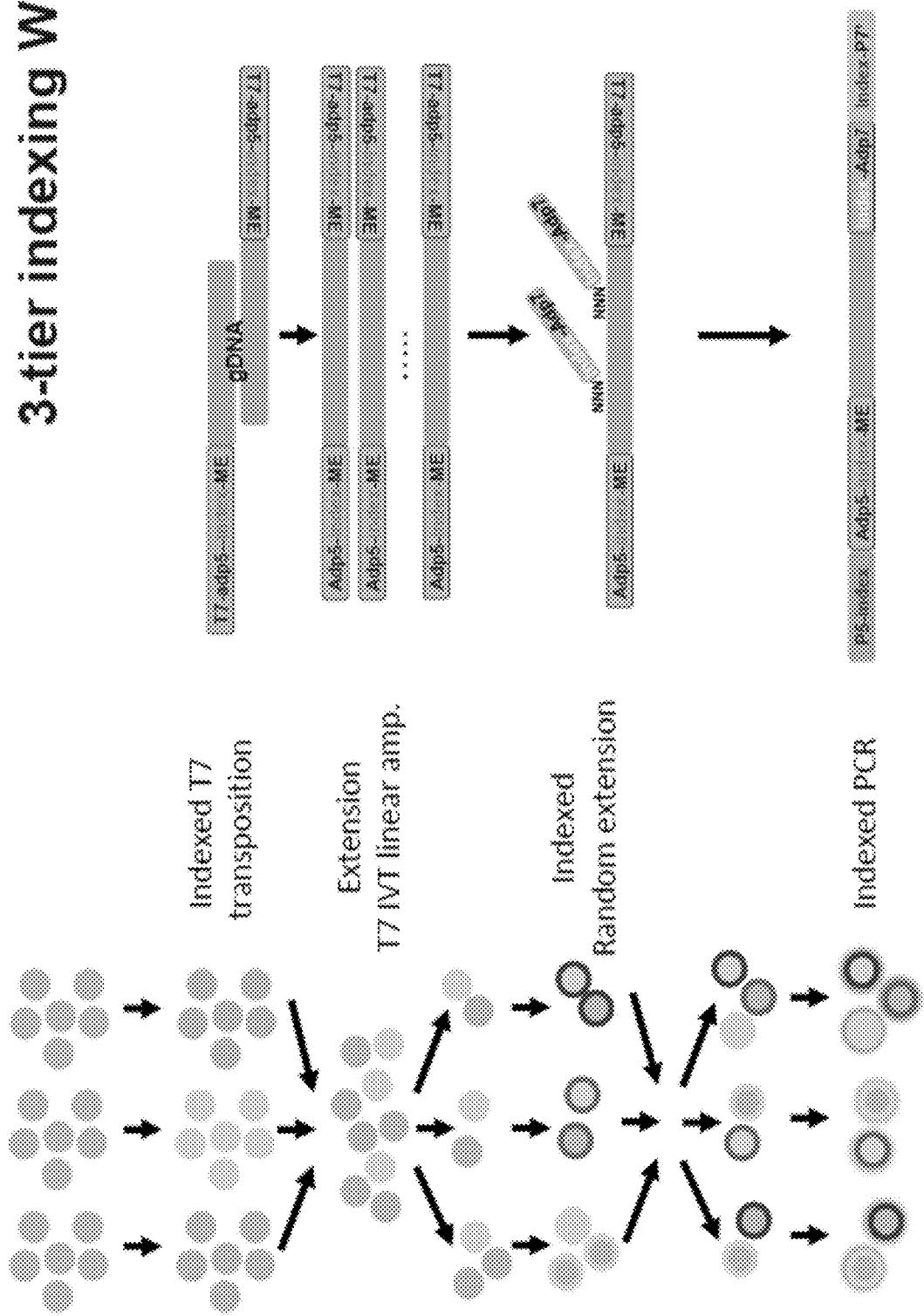
FIG. 11 is a schematic that illustrates an embodiment of a method of performing multiple co-assays on a hollow bead encapsulating a cell.

Single cell whole genome amplification was also carried out using the contiguity particles, as outlined in FIG. 11. This was done using Indexed T7 transposition of contiguity particles in individual wells followed by pooling and extension via T7 in vitro transcription (IVT) linear amplification. The beads were separated again for indexed random extension, pooled and split again for a final indexed PCR.

The contiguity particles showed efficient tagmentation when they were targeted by FAM labeled transposomes. The nuclei were stained with Hoechst (DNA stain with blue emission) while the transposed nuclei were stained fluorescent green with FAM (fluorescent dye). Lysing the cells with SDS increased the background fluorescence of contiguity particles while there was no signal seen from contiguity particles without any cells. The results demonstrate that an ATAC-seq library may be generated for cells encapsulated inside contiguity particles with only small portion of leakage of short fragments from tagmentation.

Example 3—Nucleic Acid Library Preparation in Contiguity Particles

The following example demonstrates a method for whole genome library preparation from a cell encapsulated within a contiguity particle.

Figure 12:
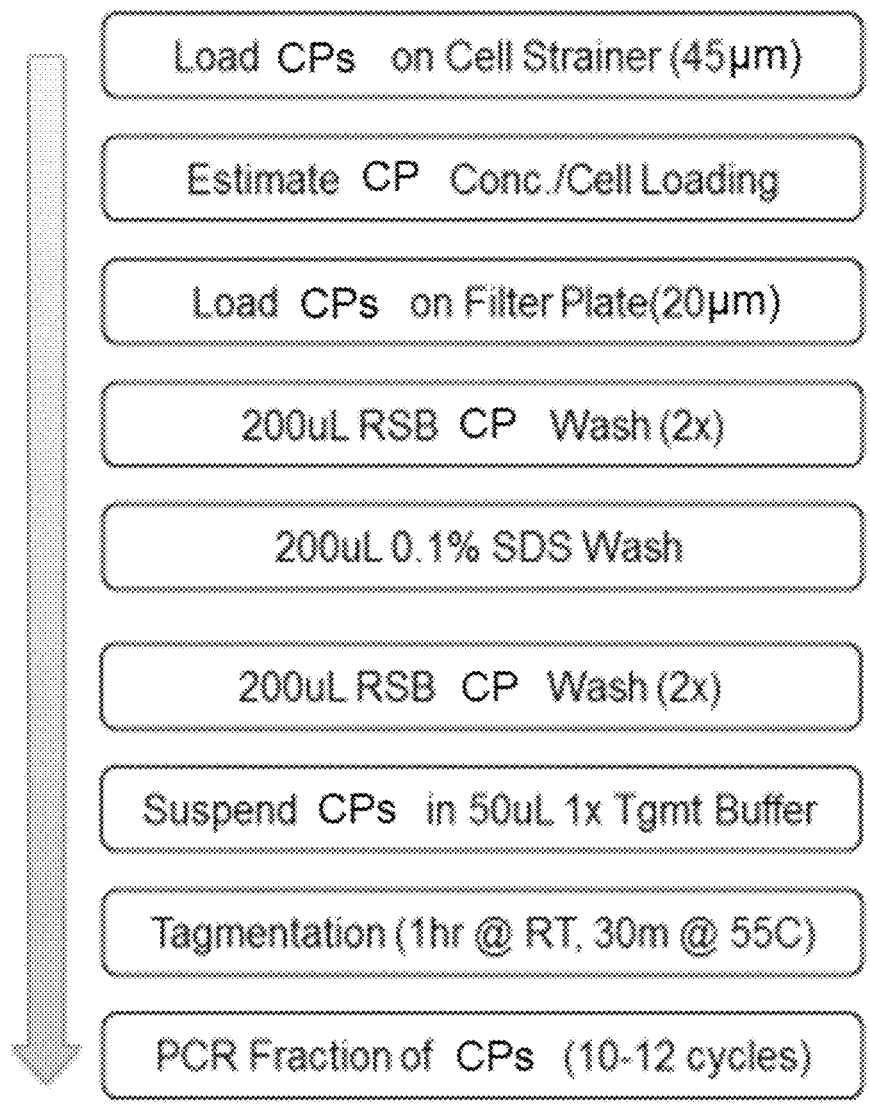
FIG. 12 is a flow diagram that illustrates an embodiment of a method of preparing a whole genome library with a hollow bead encapsulating a cell.

FIG. 12 outlines a schematic for performing whole genome library on a single cell encapsulated within a contiguity particle. As outlined in the schematic of FIG. 12, a contiguity particle was used for generating a Nextera whole genome library. Contiguity particles as prepared in Example 1 were obtained. The contiguity particles (CPs) were loaded on a 45 µm cell strainer and multiple washes with PBS or Tris-Cl were performed to remove any non-encapsulated cells. One advantage of encapsulating a cell in a contiguity particle is an improved ability to handle and process them. One simple way to do this is through use of spin columns or filter plates. The pore size of the filter may be smaller than the bead diameter. Examples of filter plates include but not limited to Millipore's MultiScreen-Mesh Filter Plates with 20, 40, and 60 µm pore size, Millipore's MultiScreen Migration Invasion and Chemotaxis Filter Plate with 8.0 µm pores, or Pall's AcroPrep Advance 96-Well Filter Plates for Aqueous Filtration with 30-40 µm pores. With these filter plates, bead encapsulated cells were easily separated from solution, allowing multiple buffer exchanges.

The washed beads were suspended in buffer and removed from the filter. To estimate the final concentration of beads, efficiency of cell loading, and to ensure that no non-encapsulated cells remained, an aliquot of the beads was visualized under microscope.

To perform Nextera tagmentation, Millipore's 20 µm Nylon Multi Screen-Mesh Filter Plates were used. To limit adhesion of beads to the filter, they were pre-wet with Pluronic F-127. After centrifugation of the plate for 30 s @ 500 g, buffer flowed through the filter will maintaining the beads. The beads were washed twice with 200 µL of Tris-Cl buffer, then suspended in lysis buffer (0.1% SDS). Beads were incubated in lysis buffer for 1 min before removal by centrifugation. To remove residual lysis buffer, two additional 200 µL Tris-Cl washes were performed. Next, cells were suspended in 45 µL of 1× Tagmentation buffer by pipetting up and down, then transferred to a strip tube. To 45 µL of beads, 5 µL of Tagmentation DNA Enzyme (TDE, Illumina Inc.) was added and incubation in a thermal cycler was performed for 1 hr @ RT, 30 minutes at 55° C. Alternatively, tagmentation could be performed on the filter plate by suspending bead-encapsulated cells in the tagmentation master mix and incubating on a heat block. After tagmentation, an aliquot of beads was stained with Hoechst dye and visualized under microscope. Visualization confirmed that DNA remains in the bead.

Tagmented beads (25 µL) were PCR amplified using Illumina's Nextera PCR MM (NPM, Illumina) and PCR primers. To the master PCR mix, 0.1% SDS was added to remove Tn5 bound to DNA. Pre-incubation was performed at 75° C. to help Tn5 removal in presence of SDS. Eleven PCR cycles were performed to generate a final library. Following PCR, libraries were purified using 0.9× SPRI, quantified using dsDNA qubit and/or BioAnalyzer, and sequenced on the MiSeq and/or NextSeq.

The method described in this example may be scaled up to perform single cell sequencing using an approach similar to sciSEQ (Vitak et al. Nat Meth. 2017; 14:302-308). For example, use of a 96-well filter plate to perform 96 indexed-tagmentation reactions simultaneously may be performed in a scale up process. After beads are added to the plate, successive buffers are added, then removed, by centrifugation or vacuum. After tagmentation, beads are collected from the filter and pooled. Pooled beads are redistributed in a second 96-well PCR plate for multiplexed PCR. In this dual level indexing scheme (Tagmentation and PCR indexing) all DNA fragments from a single bead-encapsulated cell receive the same barcode that can be deconvoluted to reconstruct the cell's genome.

The steps outlined in this example are amenable to automation on liquid handling platforms by addition of a vacuum manifold, such as Millipore's MultiScreen HTS Vacuum Manifold or Orochem's 96-well Plate Vacuum Manifold. These vacuum manifolds can be added to many liquid handling platforms, including the Biomek FX, the Microlab Star, the Tecan Genesis, etc. Tagmentation could be automated by transferring the filter plate to a thermal block. The plate is then transferred back to the vacuum manifold for post tagmentation washes.

The embodiments, examples, and figures described herein provide compositions, methods, and systems for retaining genetic material in physically confined space during the process from lysis to library generation. Some embodiments provide libraries originated from single long DNA molecule or a single cell to be released on a surface of a flow cell in confined space. Once the library from a single DNA molecule or single cell in the individual compartments are released to the surface of the flow cell, the library from each compartment gets seeded at close proximity to each other.

The term "comprising" as used herein is synonymous with "including," "containing," or "characterized by," and is inclusive or open-ended and does not exclude additional, unrecited elements or method steps.

The above description discloses several methods and materials of the present invention. This invention is susceptible to modifications in the methods and materials, as well as alterations in the fabrication methods and equipment. Such modifications will become apparent to those skilled in the art from a consideration of this disclosure or practice of the invention disclosed herein. Consequently, it is not intended that this invention be limited to the specific embodiments disclosed herein, but that it cover all modifications and alternatives coming within the true scope and spirit of the invention.

All references cited herein, including but not limited to published and unpublished applications, patents, and literature references, are incorporated herein by reference in their entirety and are hereby made a part of this specification. To the extent publications and patents or patent applications incorporated by reference contradict the disclosure contained in the specification, the specification is intended to supersede and/or take precedence over any such contradictory material.

What is claimed is:

1. A method of performing multiple sequential co-assays on a single cell encapsulated within a hollow bead, comprising:
    obtaining a hollow bead encapsulating a single cell, wherein the hollow bead comprises:
    a polymer shell comprising PEG-epoxide and amine dissolved in oil or PEG-epoxide and PEG-amine; and
    a single cell disposed within the polymer shell,
    wherein the polymer shell comprises pores that allow diffusion of reagents through the polymer shell while retaining the single cell; and
    sequentially contacting the single cell with the reagents to perform multiple sequential co-assays.

2. The method of claim 1, wherein an interior of the polymer shell comprises an aqueous environment.

3. The method of claim 1, wherein the single cell disposed within the polymer shell is free from interaction with the polymer shell and/or is not in contact with the polymer shell.

4. The method of claim 1, wherein the hollow bead has a diameter of about 20 μm to about 200 μm.

5. The method of claim 1, wherein the polymer shell comprises a four-arm polyethylene glycol (PEG).

6. The method of claim 1, wherein the single cell is a mammalian cell.

7. The method of claim 1, wherein the reagents comprise enzymes, chemicals, and primers having a size of less than 50 base pairs.

8. The method of claim 7, wherein the reagents comprise one or more of a lysozyme, proteinase K, random hexamers, polymerase, transposase, primers, ligase, catalyzing enzyme, deoxynucleotide triphosphates, buffers, or divalent cations.

9. The method of claim 1, wherein the multiple sequential co-assays comprise lysis, DNA analysis, RNA analysis, protein analysis, tagmentation, nucleic acid amplification, nucleic acid sequencing, DNA library preparation, assay for transposase accessible chromatin using sequencing (ATAC-seq), contiguity-preserving transposition sequencing (CPT-seq), single cell combinatorial indexed sequencing (SCI-seq), or single cell genome amplification, or any combination thereof performed sequentially.

10. The method of claim 1, wherein the hollow bead encapsulating a single cell is seeded on a solid support.

11. The method of claim 10, wherein the solid support is an etched surface, a well, a flow-cell device, a microfluidic channel, a bead, or a column.

* * * * *

SEQUENCE LISTING

<160> NUMBER OF SEQ ID NOS: 16

<210> SEQ ID NO 1
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 1
aatgatacgg cgaccaccga                                          20

<210> SEQ ID NO 2
<211> LENGTH: 21
<212> TYPE: DNA
<213> ORGANISM: Artificial Sequence
<220> FEATURE:
<223> OTHER INFORMATION: Synthetic Oligonucleotide

<400> SEQUENCE: 2
caagcagaag acggcatacg a                                        21

```
<210> SEQ ID NO 3
<211> LENGTH: 30
<212> TYPE: DNA
<213> ORGANISM: Artificial Sequence
<220> FEATURE:
<223> OTHER INFORMATION: Synthetic Oligonucleotide

<400> SEQUENCE: 3
tttttttttt aatgatacgg cgaccaccga                                       30

<210> SEQ ID NO 4
<211> LENGTH: 31
<212> TYPE: DNA
<213> ORGANISM: Artificial Sequence
<220> FEATURE:
<223> OTHER INFORMATION: Synthetic Oligonucleotide

<400> SEQUENCE: 4
tttttttttt caagcagaag acggcatacg a                                     31

<210> SEQ ID NO 5
<211> LENGTH: 15
<212> TYPE: DNA
<213> ORGANISM: Artificial Sequence
<220> FEATURE:
<223> OTHER INFORMATION: Synthetic Oligonucleotide B15 adaptor

<400> SEQUENCE: 5
gtctcgtggg ctcgg                                                       15

<210> SEQ ID NO 6
<211> LENGTH: 14
<212> TYPE: DNA
<213> ORGANISM: Artificial Sequence
<220> FEATURE:
<223> OTHER INFORMATION: Synthetic Oligonucleotide A14 adaptor

<400> SEQUENCE: 6
tcgtcggcag cgtc                                                        14

<210> SEQ ID NO 7
<211> LENGTH: 19
<212> TYPE: DNA
<213> ORGANISM: Artificial Sequence
<220> FEATURE:
<223> OTHER INFORMATION: Synthetic Oligonucleotide ME adaptor

<400> SEQUENCE: 7
agatgtgtat aagagacag                                                   19

<210> SEQ ID NO 8
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 8
tctacacaca ttctctgtc                                                   19

<210> SEQ ID NO 9
<211> LENGTH: 14
<212> TYPE: DNA
<213> ORGANISM: Artificial Sequence
<220> FEATURE:
<223> OTHER INFORMATION: Synthetic Oligonucleotide
```

-continued

```
<400> SEQUENCE: 9
tggtagagag ggtg                                                      14

<210> SEQ ID NO 10
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 10
tactactcac ctccc                                                     15

<210> SEQ ID NO 11
<211> LENGTH: 29
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: 16-21
<223> OTHER INFORMATION: n = a, c, t, or g
<223> OTHER INFORMATION: B15_N6_Link1

<400> SEQUENCE: 11
gtctcgtggg ctcggnnnnn ngacttgtc                                      29

<210> SEQ ID NO 12
<211> LENGTH: 47
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: 9-14
<223> OTHER INFORMATION: n = a, c, t, or g
<223> OTHER INFORMATION: Phos_Link2_A7G_ME

<400> SEQUENCE: 12
tagagcatnn nnnntggtag agagggtgag atgtgtataa gagacag                  47

<210> SEQ ID NO 13
<211> LENGTH: 28
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: 15-20
<223> OTHER INFORMATION: n = a, c, t, or g
<223> OTHER INFORMATION: A14_N6_Link1

<400> SEQUENCE: 13
tcgtcggcag cgtcnnnnnn gtaatcac                                       28

<210> SEQ ID NO 14
<211> LENGTH: 48
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: 9-14
<223> OTHER INFORMATION: n = a, c, t, or g
<223> OTHER INFORMATION: Phos_Link2_B7G_ME
```

```
<400> SEQUENCE: 14
catcatccnn nnnntactac tcacctccca gatgtgtata agagacag       48

<210> SEQ ID NO 15
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 15
atgctctaga caagt                                          15

<210> SEQ ID NO 16
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 16
ggatgatggt gatta                                          15
```